United States Patent
Hatano et al.

(10) Patent No.: US 9,964,500 B2
(45) Date of Patent: May 8, 2018

(54) DEFECT INSPECTION DEVICE, DISPLAY DEVICE, AND DEFECT CLASSIFICATION DEVICE

(71) Applicant: Hitachi High-Technologies Corporation, Minato-ku, Tokyo (JP)

(72) Inventors: Hisashi Hatano, Tokyo (JP); Koichi Nagoya, Tokyo (JP); Mamoru Kobayashi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days. days.

(21) Appl. No.: 15/531,066

(22) PCT Filed: Dec. 8, 2014

(86) PCT No.: PCT/JP2014/082419
§ 371 (c)(1),
(2) Date: May 26, 2017

(87) PCT Pub. No.: WO2016/092614
PCT Pub. Date: Jun. 16, 2016

(65) Prior Publication Data
US 2017/0328846 A1 Nov. 16, 2017

(51) Int. Cl.
*G01N 23/00* (2006.01)
*G01N 23/225* (2018.01)
(Continued)

(52) U.S. Cl.
CPC ......... *G01N 23/2251* (2013.01); *G01N 21/47* (2013.01); *G01N 21/9501* (2013.01);
(Continued)

(58) Field of Classification Search
CPC ......... G01N 23/2251; G01N 21/95607; G01N 21/9501; G01N 21/47; G01N 2223/302;
(Continued)

(56) References Cited

U.S. PATENT DOCUMENTS

| 2007/0177787 A1 | 8/2007 | Maeda et al. |
| 2011/0182496 A1 | 7/2011 | Sakai et al. |
| 2013/0077850 A1 | 3/2013 | Hirai et al. |
| 2013/0294680 A1 | 11/2013 | Harada et al. |
| 2014/0253912 A1* | 9/2014 | Honda ................. G01N 21/956 356/237.5 |

(Continued)

FOREIGN PATENT DOCUMENTS

| JP | 2007-212201 A | 8/2007 |
| JP | 2013-98267 A | 5/2013 |
| JP | 2014-149177 A | 8/2014 |
| WO | WO 2010/024064 A1 | 3/2010 |
| WO | WO 2011/155123 A1 | 12/2011 |

(Continued)

OTHER PUBLICATIONS

International Search Report (PCT/ISA/210) issued in PCT Application No. PCT/JP2014/082419 dated Mar. 17, 2015 with English-language translation (four (4) pages).

(Continued)

*Primary Examiner* — Michael Maskell
(74) *Attorney, Agent, or Firm* — Crowell & Moring LLP

(57) ABSTRACT

A defect inspection device is provided with an illumination optical system that irradiates light or an electron beam onto a sample, a detector that detects a signal obtained from the sample through the irradiation of the light or electron beam, a defect detection unit that detects a defect candidate on the sample through the comparison of a signal output by the detector and a prescribed threshold, and a display unit that displays a setting screen for setting the threshold. The setting screen is a two-dimensional distribution map that represents the distribution of the defect candidates in a three dimensional feature space having three features as the axes thereof and includes the axes of the three features and the threshold, which is represented in one dimension.

16 Claims, 17 Drawing Sheets

(51) Int. Cl.
- *G01N 21/47* (2006.01)
- *G01N 21/95* (2006.01)
- *G01N 21/956* (2006.01)
- *G01N 21/84* (2006.01)

(52) U.S. Cl.
CPC . *G01N 21/95607* (2013.01); *G01N 2021/845* (2013.01); *G01N 2223/302* (2013.01); *G01N 2223/6116* (2013.01); *G01N 2223/643* (2013.01)

(58) Field of Classification Search
CPC ....... G01N 2021/845; G01N 2223/643; G01N 2223/6116
USPC ................................. 250/306, 307, 310, 311
See application file for complete search history.

(56) References Cited

U.S. PATENT DOCUMENTS

2015/0369752 A1\* 12/2015 Honda ............... G01N 21/8851 356/237.2

FOREIGN PATENT DOCUMENTS

| WO | WO 2012/098615 A1 | 7/2012 | |
|---|---|---|---|
| WO | WO 2014119376 A1 \* | 8/2014 | ......... G01N 21/8851 |

OTHER PUBLICATIONS

Japanese-language Written Opinion (PCT/ISA/237) issued in PCT Application No. PCT/JP2014/082419 dated Mar. 17, 2015 (three (3) pages).

\* cited by examiner

| | | DEFECT INFORMATION | | TOTAL |
|---|---|---|---|---|
| | | NECESSARY | UNNECESSARY | |
| RESULT OF DEFECT JUDGEMENT | NECESSARY | 80 | 5 | 85 |
| | UNNECESSARY | 4 | 70 | 74 |
| | TOTAL | 84 | 75 | 159 |

UNIT OF NUMBER IN TABLE = NO. OF PCS   ACCURACY RATE = 94% (150/159)

DEFECT INSPECTION DEVICE, DISPLAY DEVICE, AND DEFECT CLASSIFICATION DEVICE

TECHNICAL FIELD

The present invention relates to a technology for displaying a threshold setting screen when a defect of a sample is inspected or classified.

BACKGROUND ART

In a semiconductor manufacturing process, a defect, such as a scratch or a foreign substance, on a wafer affects the yield of products. Accordingly, to detect a defect on a wafer, feed it back to the semiconductor manufacturing process, and manage the detected defect is important in managing the yield. What is used to detect such a defect is a so-called inspection device.

In an inspection device, a threshold (or a threshold plane) used when detecting a defect is placed on a defect feature space. Furthermore, by classifying the type of the detected defect, more accurate yield management can be achieved. As a prior art relating to the setting of a threshold for detecting a defect, PTL 1 is cited.

CITATION LIST

Patent Literature

PTL 1: JP 2014-149177 A

SUMMARY OF INVENTION

Technical Problem

In defect inspection for managing the yield, appropriate defect judgment is required. For defect judgment, a threshold (for example, a threshold plane) on a defect feature space needs to be set appropriately. This threshold for defect judgment is generally set by a user.

Conventionally, when a threshold is set, information on a defect that a user has judged in advance (a result of determination whether each defect candidate is the defect the user needs or the defect the user does not need) is used. For example, referring to a result of comparison between this defect information and a result of judgment of the defect based on the set threshold, the user determines if appropriate defect judgment can be made by the set threshold.

In a case of the above-described threshold setting method, the user refers to only a result of comparison, and therefore cannot grasp a relationship between the set threshold and the distribution of defect candidates. Therefore, when the set threshold is not appropriate, there is no guideline for how to change the threshold, and the resetting or adjustment of the threshold is difficult. Therefore, it requires information serving as a guideline for the resetting or adjustment of the threshold. Incidentally, as is the case for defect judgment, also when the type of a defect is classified, a threshold (for example, a boundary plane for classification) for each type (category) on a feature space is set, and therefore the same problem is present.

Accordingly, the present invention provides a display technology enabling to grasp a relationship between a threshold and the distribution of defect candidates in the setting of a threshold for defect detection or defect classification.

Solution to Problem

In order to solve the problem, the configurations described in claims may be employed. The present application includes solutions to the problem, and for example, one of the solutions provides a defect inspection device including: an illumination optical system that irradiates a sample with a light or an electron beam; a detector that detects a signal obtained from the sample by irradiation with the light or the electron beam; a defect detecting unit that detects defect candidates on the sample by comparing a signal output from the detector with a predetermined threshold; and a display unit that displays a setting screen for setting the threshold, wherein the setting screen is a two-dimensional distribution diagram that represents a distribution of defect candidates in a three-dimensional feature space with three features as axes and includes the axes of three features and the threshold represented in one dimension.

Furthermore, according to another example, there is provided a display device that displays thereon information on a defect candidate from a defect inspection device. The display device includes a display unit that displays thereon a setting screen for setting a threshold for judgement of the defect candidate; the setting screen is a two-dimensional distribution diagram that represents the distribution of defect candidates in a three-dimensional feature space with three features as axes and includes the axes of three features and the threshold represented in one dimension.

Furthermore, according to another example, there is provided a defect inspection device including: an illumination optical system that irradiates a sample with a light or an electron beam; a detector that detects a signal obtained from the sample by irradiation with the light or the electron beam; a defect classifying unit that classifies a defect on the sample by comparing a signal output from the detector with at least one threshold; and a display unit that displays a setting screen for setting the threshold, wherein the setting screen is a two-dimensional distribution diagram that represents a distribution of defect candidates in a three-dimensional feature space with three features as axes and includes the axes of three features and the threshold represented in one dimension.

Advantageous Effects of Invention

According to the present invention, it is possible to grasp a relationship between a threshold and the distribution of defect candidates in the setting of a threshold for defect detection or defect classification, which facilitates the setting or adjustment of the threshold.

Further characteristics relevant to the present invention shall be revealed by description of the present specification and accompanying drawings. Furthermore, problems, configurations, and advantageous effects other than the above are revealed by the following description of embodiments.

DESCRIPTION OF EMBODIMENTS

Embodiments of the present invention are described below with reference to accompanying drawings. Incidentally, the accompanying drawings show specific examples in accordance with the principle of the invention; however, these are for understanding of the invention, and are never used for interpreting the invention in a limited way. Combinations of the following embodiments and known arts and variations resulting from replacement are also included in the scope of the invention.

The following embodiments relate to a method for displaying a feature space required to set a threshold for detecting or classifying a defect of a sample.

In the present specification, a "defect" covers any defect that affects the yield of products in a manufacturing process. For example, a defect includes not only structural failure on a sample (for example, a semiconductor wafer) but also a foreign substance present in a sample.

Furthermore, in the present specification, a "feature" is information representing the likelihood of a defect. A feature includes not only information representing a feature of a detection signal obtained from a detection system to be described below but also information representing a feature obtained by performing predetermined processing (for example, image processing, calculation processing, statistical processing, etc.) on the detection signal. As an example of a feature, there are brightness information of a detection signal, information on an image obtained from a detection signal, etc.

[First Embodiment]

Figure 1:
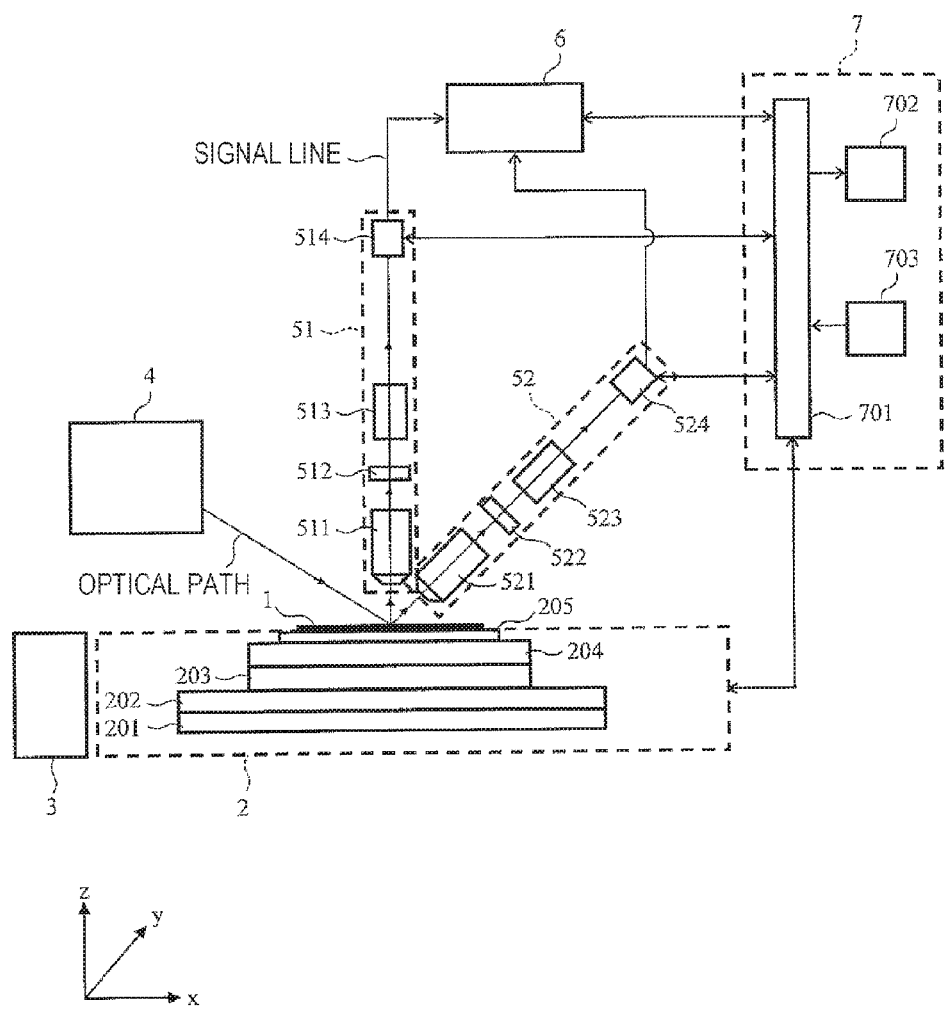
FIG. 1 is a block diagram showing a schematic configuration of a defect inspection device in a first embodiment.

FIG. 1 is a block diagram showing a schematic configuration of a defect inspection device in a present embodiment. The defect inspection device includes, as main components, samples 1, a stage 2, a wafer conveying system 3, an illumination optical system 4, detection optical systems 51 and 52, a processing system 6, and a control system 7.

A sample 1 (for example, a semiconductor wafer) that is an object to be inspected is loaded from the wafer conveying system 3 including a wafer pod and a prealigner onto the stage 2 by a robot arm. Incidentally, at least one of objects to be inspected can include a bare wafer, a patterned wafer, a film-coated wafer, or another sample.

The stage 2 can move the sample (the wafer) 1 in an x direction and a y direction virtually perpendicular to the x direction and rotate the wafer 1 at a predetermined angle. The stage 2 includes a chuck 205 for adsorbing the wafer 1, a y stage 201 for moving the wafer 1 in the y direction, an x stage 202 for moving the wafer 1 in the x direction, a z stage 203 for moving the wafer 1 in a z direction to change the level of the wafer 1, and a θ stage 204 for rotating the wafer 1. Incidentally, the stage 2 can have any form, and does not have to have all of the x-, y-, z-, and θ-axis stages. The following embodiment can be also applied to an inspection device that does not have all of the x-, y-, z-, and θ-axis stages.

The illumination optical system 4 is for forming an illumination area in the sample 1, and includes a light source, a mirror, and a lens. The illumination area may virtually be a point, or may virtually be a line. The light source can be any one as long as it emits any optical light, such as white light, ultraviolet light, wavelength-controlled light, or photon beams such as laser light. Illumination conditions (for example, an emission angle, an illumination direction, an illumination wavelength, a polarization state, etc.) of the illumination optical system 4 are selected by a user or are automatically selected, and these illumination conditions are controlled through the control system 7. Incidentally, the following embodiment can be also applied to a defect inspection device using charged particle radiation (for example, electron beams).

A scattered light from the illumination area is detected by the detection optical systems 51 and 52. The number of detection optical systems can be two just like this embodiment, or three or more detection optical systems can be included. Or, it can be configured to provide one detection optical system.

Here we describe a detection method taking the detection optical system 51 as an example. The detection optical system 51 includes an objective lens 511, a spatial filter 512, an imaging lens 513, and a sensor 514. A scattered light from the illumination area is collected by the objective lens 511, and, of the collected light, an undesired light is blocked by the spatial filter 512. A light passed through the spatial filter 512 is focused onto the sensor 514 by the imaging lens 513. This detection method is the same for the detection optical system 52. Likewise, the detection optical system 52 includes an objective lens 521, a spatial filter 522, an imaging lens 523, and a sensor 524.

Signals from the sensors 514 and 524 are each transmitted to the processing system 6. The processing system (a defect detecting unit) 6 compares the signals from the sensors 514 and 524 with a predetermined threshold, and performs inspection (detection of a defect candidate). Using a result of the inspection (the presence or absence of a defect) and a movement signal of the stage 2, the processing system 6 associates the detected defect with its coordinates on the wafer 1, and sends defect detection information (a defect map) to control system 7. The defect map here is a map representing which position on the sample 1 the defect is in.

The control system 7 includes a control unit 701 that issues an instruction to a part in the device and receives information from the part, a display unit 702 that outputs various information, and an input unit 703 for performing an input to the defect detection device.

Incidentally, the processing system 6 and the control system 7 are composed of an information processing apparatus (a computer) including a processor (not shown), a memory (not shown), etc. The processor executes processes, which correspond to respective components of the processing system 6 and the control system 7 to be described later, in accordance with instructions of a program stored in the memory. That is, respective components of the processing system 6 and the control system 7 can be realized as software. Incidentally, part of the processing system 6 and the control system 7 can be implemented as hardware.

The display unit 702 is, for example, a display or the like connected to an information processing apparatus. Incidentally, information output to the display unit 702 can be output to another device using a communication means. The input unit 703 is, for example, a keyboard and mouse connected to the information processing apparatus. Incidentally, input information from the input unit 703 can be input from another device through a communication means.

An example of the defect inspection device is described above; however, the defect inspection device can have another configuration other than that described above, and, for example, can be an inspection device having no spatial filter.

Figure 2:
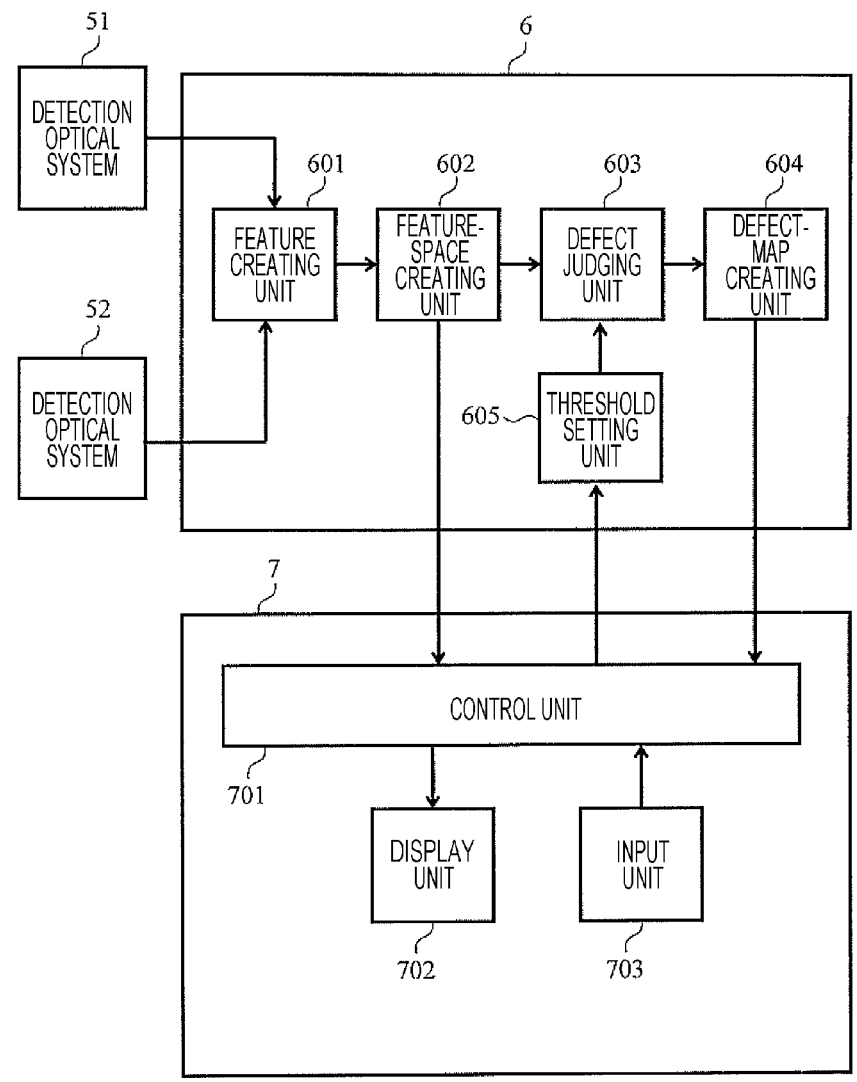
FIG. 2 is a block diagram showing a configuration of a part involved in defect inspection in the first embodiment.

FIG. 2 is a block diagram showing a configuration of a part involved in defect inspection in the present embodiment. The processing system 6 includes a feature creating unit 601, a feature-space creating unit 602, a defect judging unit 603, a defect-map creating unit 604, and a threshold setting unit 605.

Figure 3:
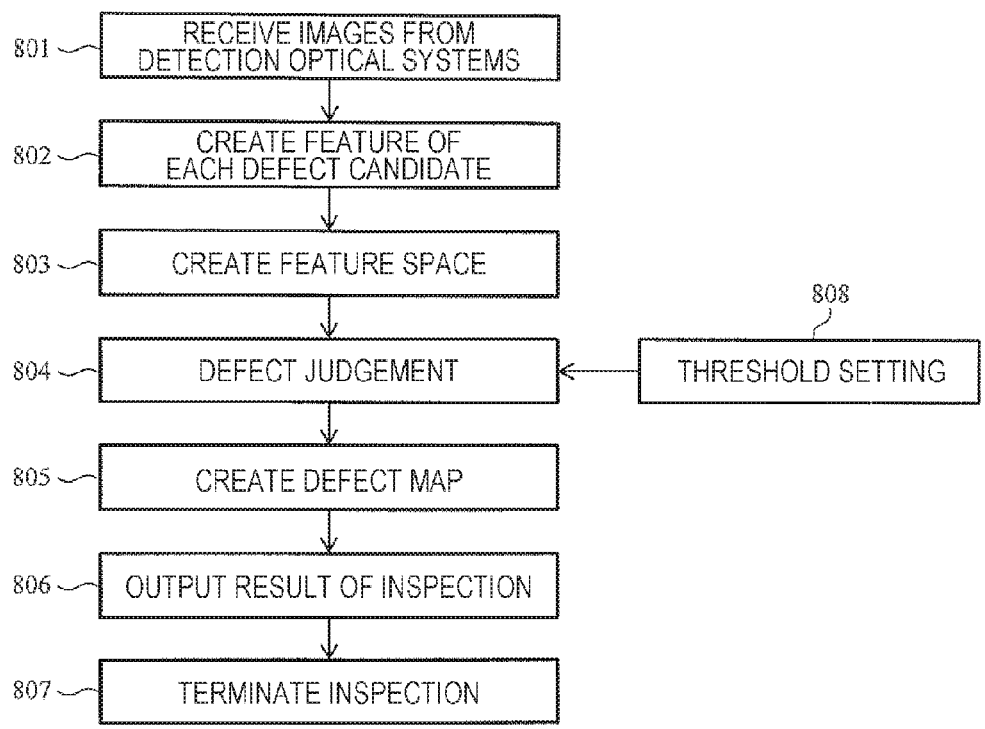
FIG. 3 is a defect inspection flow diagram in the first embodiment.

FIG. 3 is a defect inspection flow diagram in the present embodiment. In the following description, the functional block in FIG. 2 is described as the subject; however, since a program is executed by the processor, thereby performing a defined process by means of the memory, a communication port, etc., the processor can be described as the subject.

The feature creating unit 601 receives signals (for example, image signals) from the sensors 514 and 524 of the detection optical systems 51 and 52 (801).

Next, the feature creating unit 601 creates a feature of each defect candidate on the basis of the image signals from the detection optical systems 51 and 52 (802). Defect candidates include false detection of a noise or the like and a nuisance that a user does not intend to detect besides a defect that the user intends to detect. As for a feature of each defect candidate, there may be one feature in one defect candidate, or there maybe multiple features in one defect candidate. Here, there is described an example in which three features (feature 1, feature 2, and feature 3) are obtained from one defect candidate.

Next, the feature-space creating unit 602 creates a feature space on the basis of the feature of each defect candidate (803). The feature space here means a space in which, for example, with three axes, feature axes of feature 1, feature 2, and feature 3 are set, and defect candidates are placed on a three-dimensional space according to their values of feature 1, feature 2, and feature 3. As a matter of course, the number of features is not limited to three.

Next, the user sets a threshold (808). The input of the threshold is performed, for example, by use of the display unit 702 and the input unit 703 of the control system 7. The threshold setting unit 605 receives the threshold from the control unit 701, and outputs the threshold to the defect judging unit 603. Details of step 808 will be described later.

Next, the defect judging unit 603 performs defect judgement on the feature space created in step 803 (804). Through this defect judgement, false detection and nuisances are separated, and a defect that the user intends is extracted. At this time, the defect judging unit 603 uses the threshold set in advance in step 808 to perform the defect judgement.

Next, using a movement signal of the stage 2 acquired at the time of inspection, the defect-map creating unit 604 associates the defect judged in step 804 with its coordinates on the sample 1, and creates a defect map (805). Next, the control unit 701 receives the defect map, and outputs the defect map as a result of inspection to the display unit 702 (806). Accordingly, the inspection is terminated (807).

Figure 4A:
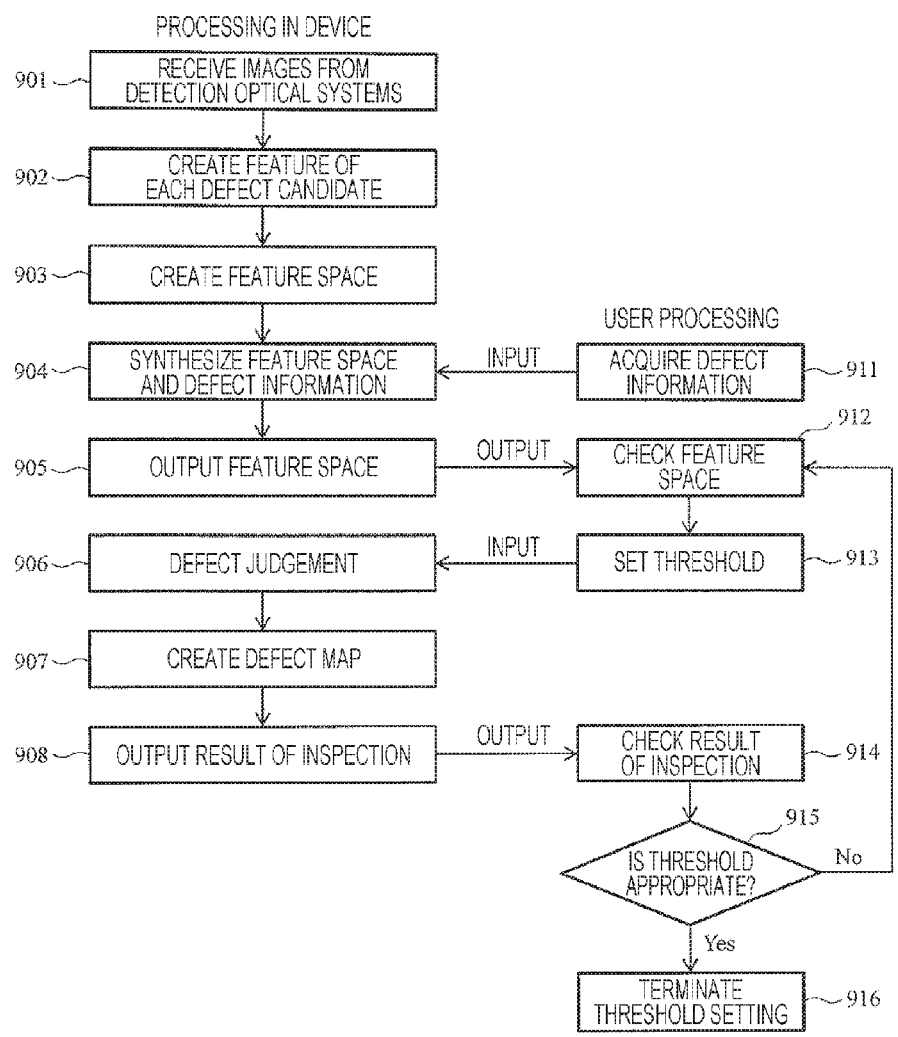
FIG. 4A is a flow diagram of threshold setting in the first embodiment.

FIG. 4A is a flow diagram showing the details of the threshold setting (step 808) in FIG. 3. Steps 901, 902, and 903 are identical to steps 801, 802, and 803 in FIG. 3. Therefore, the flow of step 904 onwards is explained.

The user inputs defect information by using the input unit 703 or another input means (911). This defect information is what whether each defect candidate is a defect to be detected or a defect not to be detected (false detection, a nuisance, or the like) by the user has been determined in advance. In other words, the defect information is information on a result of determination whether each defect candidate is the defect the user has determined to need or the defect the user has determined not to need. Incidentally, the defect information is information in which a defect candidate is associated with a result of determination of the defect candidate and coordinates on the sample 1.

As a method for obtaining this defect information, for example, there is a method to determine by observation with a scanning electron microscope (SEM). Furthermore, as an example of another method for obtaining defect information, there is a method for the user to determine from images obtained from a single or multiple detection systems in the present embodiment and create defect information in advance.

Next, the control unit 701 synthesizes the defect information input in step 911 into each defect candidate placed on the feature space created in step 903, and reconstructs the feature space (904).

Next, the control unit 701 outputs the feature space reconstructed in step 904 to the display unit 702 (905). Next, the user checks the feature space displayed on the display unit 702 (912).

Next, the user sets a threshold on the feature space by use of the input unit 703 and the display unit 702 (913). The control unit 701 outputs the set threshold to the threshold setting unit 605 of the processing system 6. The threshold setting unit 605 receives the threshold from the control unit 701, and outputs the threshold to the defect judging unit 603.

For example, in a case of a three-dimensional feature space of three features, the threshold here can be represented as a two-dimensional plane (a threshold plane) on a three-dimensional space. This threshold plane can be set as a flat surface on the feature space, or can be set as a curved surface. In a case where the threshold plane is set as a flat surface, there are advantages that the number of parameters to be set is fewer than that in a case where the threshold plane is set as a curved surface, so it is easier to set. In the case where the threshold plane is a curved surface, the threshold plane can be set more finely, and it is possible to separate the defect candidate the user needs and other defect candidates in more detail.

Next, the defect judging unit 603 performs defect judgement by use of the threshold set in step 916 (906). In the defect judgement, with the threshold as the boundary, the defect candidates are divided into necessary defect candidates and unnecessary defect candidates. The defect judging unit 603 outputs a result of this defect judgement to the defect-map creating unit 604.

Next, the defect-map creating unit 604 associates the result of defect judgement with coordinates on the sample 1, thereby creating a defect map (a result of inspection) (907). The defect-map creating unit 604 outputs the created defect map to the control unit 701. The control unit 701 outputs the result of inspection to the display unit 702 (908). In the output of this result of inspection, the result of judgement created in step 906 and the defect information input in step 911 are also simultaneously output to the display unit 702.

Figures 5, 6A:
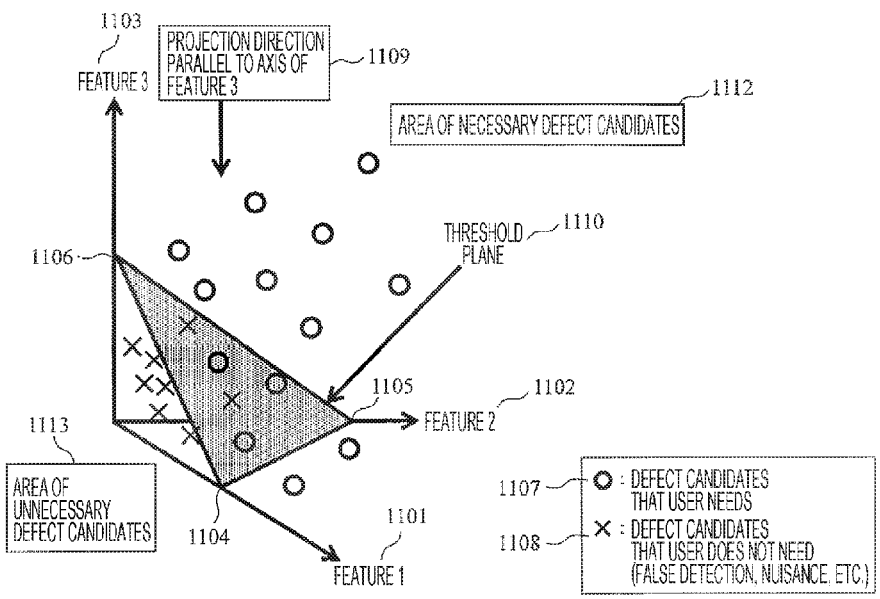
FIG. 5 is a table used to determine whether the setting of a threshold is appropriate.
FIG. 6A is a diagram of a feature space used for confirmation when the threshold in the first embodiment is set.

Next, the user checks the result of inspection (914). Next, the user checks if the defect information (the result of determination whether each defect candidate is the defect the user needs or the defect the user does not need) input in step 911 is consistent with the result of judgement in step 906, and judges if the threshold is appropriate. Incidentally, in regard to the judgement of consistency here, a comparison table in FIG. 5 is displayed on the display unit 702. Incidentally, the defect information does not have to be completely consistent with the result of judgement. If the defect information is consistent with the result of judgement in a desired proportion or more, the user judges that the defect information is consistent with the result of judgement (915).

If the consistency between the defect information and the result of judgement is less than the desired proportion, the feature space is checked again (912). Then, the setting of the threshold is performed again (913). After that, steps 906, 907, 908, and 914 are performed. In step 915, if the defect information is consistent with the result of judgement in the desired proportion or more, the threshold setting is terminated (916). Accordingly, the threshold set in step 913 is used as a threshold for inspection.

Figure 4B:
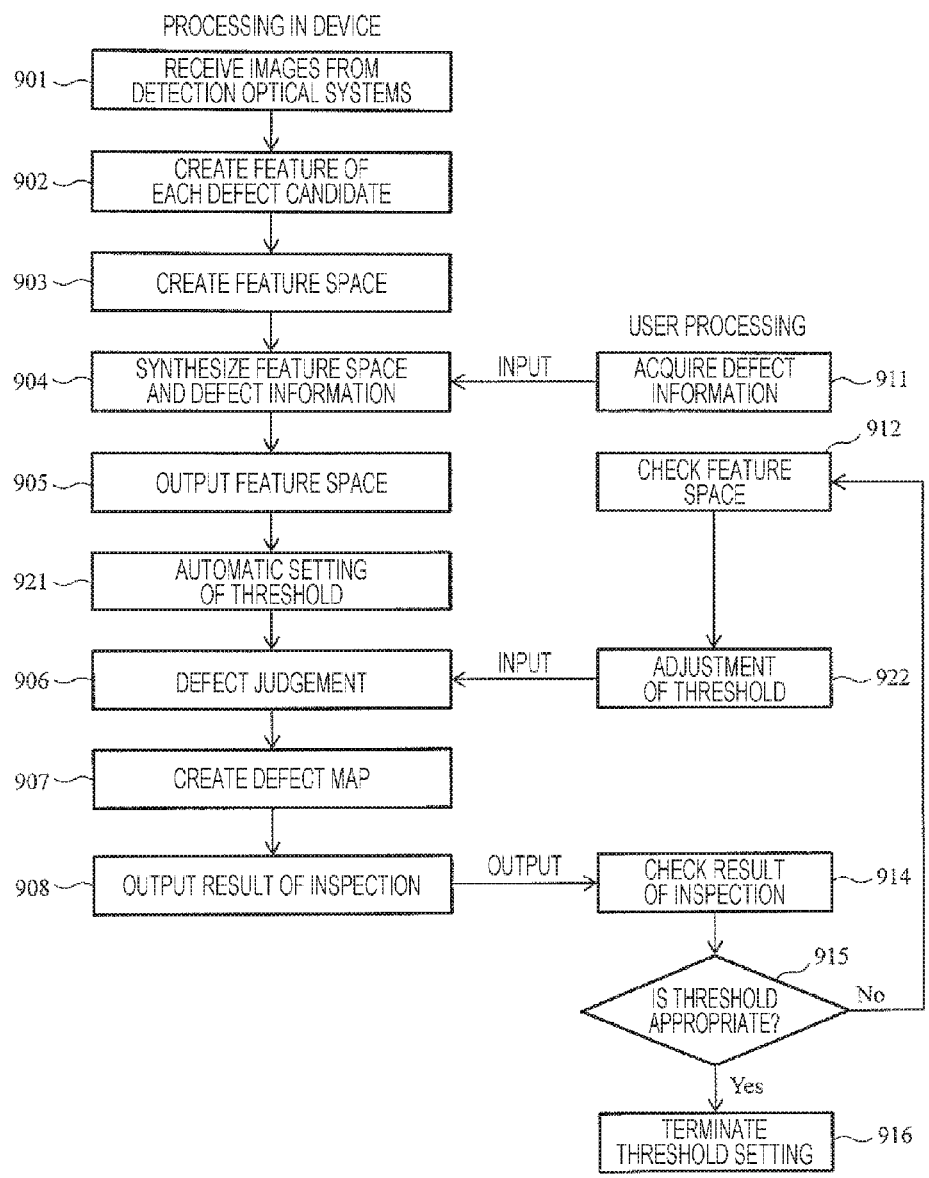
FIG. 4B is a variation of the flow diagram of the threshold setting in the first embodiment.

FIG. 4B is a variation of the flow of the threshold setting in FIG. 4A. This variation includes a step in which the threshold setting is performed not manually but automatically. Steps 901 to 905, 907, 908, and 914 to 916 are identical to those in FIG. 4A.

In this example, instead of the step in which the user sets the threshold (steps 905, 912, and 913 in FIG. 4A), the threshold setting unit 605 automatically sets the threshold (921). As a method for automatic setting of the threshold, the threshold of each feature is randomly changed, and the threshold at the point when the accuracy rate described in FIG. 5 has exceeded a predetermined proportion can be set as a threshold of the feature. Furthermore, as another example, a range of the threshold of each feature is set in advance, and the threshold is changed within the range, and then the threshold at the point when the accuracy rate described in FIG. 5 has reached a maximum can be set as a threshold of the feature.

After the automatic setting of the threshold, the defect judging unit 603 performs defect judgement by use of the set threshold (906). With the threshold as the boundary, the defect judging unit 603 divides the defect candidates into necessary defect candidates and unnecessary defect candidates. The defect judging unit 603 outputs a result of this defect judgement to the defect-map creating unit 604.

Next, the defect-map creating unit 604 creates a defect map (a result of inspection) on the basis of the result of defect judgement. The defect-map creating unit 604 outputs the created defect map to the control unit 701 (907). The control unit 701 outputs the defect map to the display unit 702. In the output of this result of inspection, the result of judgement created in step 906 and the defect information input in step 911 are also simultaneously output to the display unit 702.

Next, the user checks the result of inspection (914). Next, the user checks if the defect information (the result of determination whether each defect candidate is the defect the user needs or the defect the user does not need) input in step 911 is consistent with the result of judgement in step 906, and judges if the threshold is appropriate (915).

If the defect information is not consistent with the result of judgement, the feature space is checked (912), and the adjustment of the threshold is performed (922). After that, steps 906 to 908 and 914 to 915 are performed. In step 915, if the defect information is consistent with the result of judgement, the threshold setting is terminated (916). Accordingly, the threshold set in step 922 is used as a threshold for inspection.

FIG. 5 is a comparison table used to determine whether or not the setting of the threshold is appropriate. A comparison table 1000 is a comparison table showing the degree of consistency between the defect information input in step 911 and the result of judgement created in step 906. The comparison table 1000 can be displayed on the display unit 702 during the period from when the user checks the result of inspection and till when the threshold is set (in steps 912 and 914, step 913 in FIG. 4A, step 922 in FIG. 4B, etc.).

The comparison table 1000 enables the number of consistencies between defect information and a result of judgement and the number of inconsistencies to be grasped, and is not limited to the display in FIG. 5 as long as it can draw such a comparison.

The comparison table 1000 is output to the display unit 702 together with the result of inspection in step 908. The control unit 701 creates the comparison table 1000 by use of the result of judgement created in step 906 and the defect information input in step 911, and outputs the comparison table 1000 to the display unit 702. Furthermore, the control unit 701 is configured to update the comparison table 1000 according to the change of the threshold in step 913 or step 922 and output the updated comparison table 1000 to the display unit 702.

Here we explain about numbers (No. of pcs) displayed in cells 1001 to 1009 in the comparison table 1000.

The cell 1009 (159 pcs) shows the total count of defect candidates. A result of defect judgement (=an item 1014) corresponds to the result of judgement in step 906. Through the judgement process in step 906, the defect candidates are divided into necessary defect (=an item 1015) and unnecessary defect (=an item 1016). The total number of defect candidates that the defect judging unit 603 has judged to be necessary or unnecessary is a number in a total 1013 (the total number 1007 of defect candidates judged to be necessary=85 pcs, the total number 1008 of defect candidates judged to be unnecessary=74 pcs).

Defect information (=an item 1010) corresponds to the defect information input in step 911 (i.e., the defect information that the user has determined). For example, by observation with a SEM or the like, multiple defects on a sample are divided into user's necessary defect (=an item 1011) and unnecessary defect (=an item 1012). The total number of defect candidates that the user has determined to be necessary or unnecessary is a number in a total 1017 (the total number 1003 of defect candidates determined to be necessary=84 pcs, the total number 1006 of defect candidates determined to be unnecessary=75 pcs).

A number (80 pcs) in the cell 1001 is the number of defect candidates that the user has determined to be necessary and the defect judging unit 603 also has judged to be necessary. This defect candidate is a defect candidate of which the user's determination is consistent with a result of judgement by the defect judging unit 603 and that appropriate judgement thereof has been made.

A number (4 pcs) in the cell 1002 is the number of defect candidates that the user has determined to be necessary and the defect judging unit 603 has judged to be unnecessary. This defect candidate is judged to be unnecessary by the defect judging unit 603 even though the user has determined to be necessary, so is a defect candidate that inappropriate judgement thereof has been made (overlooking of a defect).

A number (5 pcs) in the cell 1004 is the number of defect candidates that the user has determined to be unnecessary and yet the defect judging unit 603 has judged to be necessary. This defect candidate is judged to be necessary by the defect judging unit 603 even though the user has determined to be unnecessary, so is a defect candidate that inappropriate judgement thereof has been made (false detection of a defect).

A number (70 pcs) in the cell 1005 is the number of defect candidates that the user has determined to be unnecessary and the defect judging unit 603 has judged to be unnecessary. This defect candidate is a defect candidate of which the user's determination is consistent with a result of judgement by the defect judging unit 603 and that appropriate judgement thereof has been made.

In this example, the number of defect candidates that appropriate judgement thereof has been made is the cell 1001 (80 pcs)+the cell 1005 (70 pcs)=150 pcs. The number of defect candidates that inappropriate judgement thereof has been made is the cell 1002 (4 pcs)+the cell 1004 (5 pcs)=9 pcs. Therefore, in this example, the proportion of defect candidates that appropriate judgement thereof has been made by the defect judging unit 603 is 150 pcs/159 pcs=94%. This proportion is displayed as an accuracy rate 1018.

For example, judgement of whether or not an appropriate threshold is set is assumed to be performed by use of a criterion that "the proportion of defect candidates that appropriate judgement thereof has been made is 80% or more." In this example, the proportion of defect candidates that appropriate judgement thereof has been made is 94%, so it is judged that an appropriate threshold has been set.

On the other hand, if the proportion of defect candidates that appropriate judgement thereof has been made is less than 80%, the above criterion is not met. In this case, the resetting of the threshold (step 913) or the adjustment of the threshold (step 922) needs to be performed. However, a method of determining whether or not the setting of the threshold is appropriate is not limited to the method using the comparison table 1000 in FIG. 5.

FIG. 6A is a diagram used when a feature space is checked (step 912). The feature space in FIG. 6A is created by the control unit 701. The control unit 701 synthesizes a feature space created by the feature-space creating unit 602 and defect information input by the user with the input unit 703, thereby creating the feature space. This feature space is output, as one of setting screens, to the display unit 702.

While checking this feature space, the user performs the setting of the threshold in step 913 in FIG. 4A or the adjustment of the threshold in step 922 in FIG. 4B.

On this feature space, multiple defect candidates are placed. Defect candidates determined to be necessary by the user are displayed by a mark (○), and defect candidates determined to be unnecessary by the user are displayed by a mark (×).

FIG. 6A is based on the assumption that defect judgement (step 804 or step 906) is performed by use of three features. However, the number of features used in defect judgement is not necessarily three, and may be four or more. In a case of using four or more features, three features likely to contribute to the defect judgement can be selected from multiple features and displayed. Also in a display method described below, defect judgement using three features is assumed; however, it can be displayed in judgement using four or more features as well.

The three features are created by the feature creating unit 601 by use of signals from the detection optical systems 51 and 52. The feature creating unit 601 can create the three features by using signals from three different detection optical systems, or can create the three features by using a signal from one detection optical system. Furthermore, the feature creating unit 601 can create the three features by a combination of multiple signals from multiple detection optical systems.

FIG. 6A is a diagram where feature 1 (1101), feature 2 (1102), and feature 3 (1103) are assigned to three axes, respectively, and each defect candidate is placed on a three-dimensional space on the basis of values of the three features. The placed defect candidate is added with defect information input by the user. That is, defect candidates are output to the display unit 702 so that defect candidates 1107 that the user needs and defect candidates (false detection, a nuisance, and the like) 1108 that the user does not need are distinguishable. In FIG. 6A, they are distinguished by the marks "○" and "×"; however, they can be distinguished by the display color, or can be distinguished by the size of a dot indicating a defect candidate.

A threshold plane 1110 is defined by intercepts 1104, 1105, and 1106 on the feature axes. The threshold plane 1110 divides the feature space in two, and is defined by a two-dimensional plane in the three-dimensional feature space. Defect candidates on this space are separated into necessary defect candidates and unnecessary defect candidates by the threshold plane 1110. Defect candidates present in an area 1112 (an area on the upper side of the threshold plane 1110), which is one of the two separated areas, are judged to be necessary defect candidates, and defect candidates present in an area 1113 (an area on the lower side of the threshold plane 1110), which is the other area, are judged to be unnecessary defect candidates. Defect judgement is performed by this spatial separation (step 804 or step 906).

In this example, the defect judging unit 603 judges defect candidates in the area 1112 on the upper side of the threshold plane 1110 as a necessary defect. In the defect judgement, a defect candidate in the area on the lower side of the threshold plane may be judged as a necessary defect according to the feature.

Figure 6B:
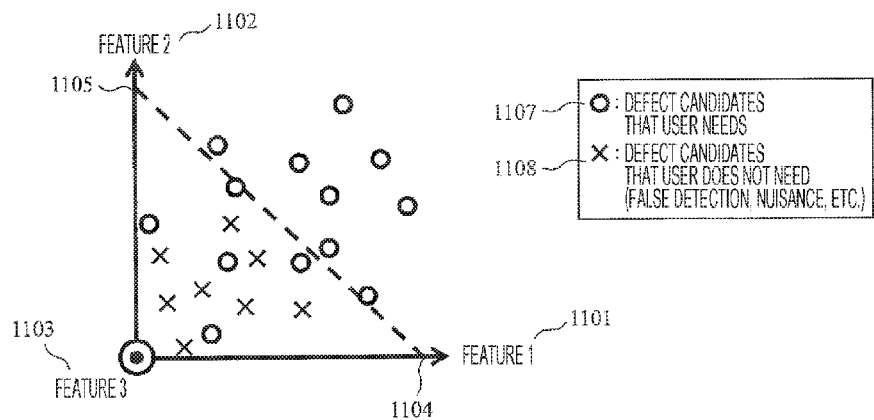
FIG. 6B is a two-dimensional distribution diagram used for confirmation when the threshold in the first embodiment is set.

FIG. 6B is a diagram that the feature space in FIG. 6A is projected onto a two-dimensional plane. The projection is in a projection direction 1109 parallel to the axis of feature 3 in FIG. 6A. As shown in FIG. 6B, a result of the projection is a diagram where defect candidates are placed in a two-dimensional plane based on feature 1 and feature 2. Here, the value of feature 3 is ignored.

In this FIG. 6B, the value of feature 3 is ignored, so the result of projection onto a two-dimensional plane does not reflect the spatial separation state on the three-dimensional space. That is, in the projected plan of FIG. 6B, the threshold plane 1110 is not virtually reflected (the user can recognize only a line connecting the intercepts 1104 and 1105), so it is difficult to determine whether or not the threshold is appropriate in the three-dimensional feature space. Particularly, the user cannot grasp the association between the accuracy rate 1018 in FIG. 5 and the projected plan of FIG. 6B in step 915 of determining whether or not the threshold (the threshold plane) is appropriate, and, in the projected plan, a guideline for which feature and how much the threshold of the feature are to be adjusted cannot be obtained. Therefore, it is difficult to set the threshold (the threshold plane) by using this projected plan.

Figure 7A:
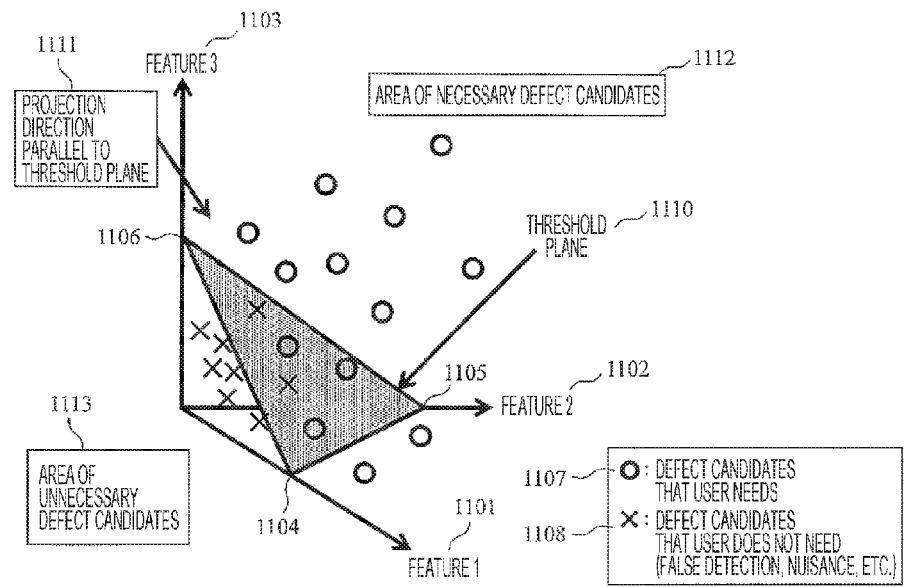
FIG. 7A is a diagram of a feature space used for confirmation when the threshold in the first embodiment is set.
Figure 7B:
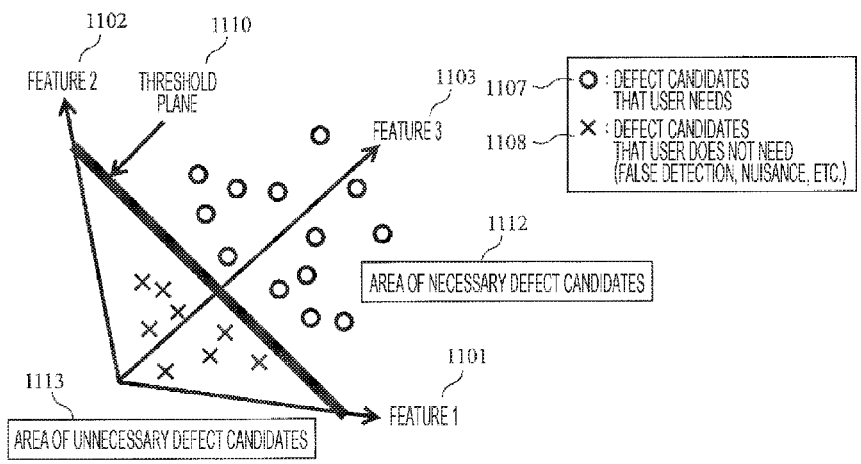
FIG. 7B is a two-dimensional distribution diagram used for confirmation when the threshold in the first embodiment is set.

In the present embodiment, there is proposed a feature-space display method that solves this problem. FIGS. 7A and 7B are diagrams used when a feature space is checked (step 912). While checking setting screens in FIGS. 7A and 7B, the user performs the setting of the threshold in step 913 in FIG. 4A or the adjustment of the threshold in step 922 in FIG. 4B.

Here we explain differences from FIGS. 6A and 6B. FIG. 7B is a projected plan where the projection onto a two-dimensional plane is performed from a projection direction (1111) parallel to the threshold plane.

A feature space in FIG. 7A is created by the control unit 701. The control unit 701 synthesizes a feature space created by the feature-space creating unit 602 and defect information input by the user with the input unit 703, thereby creating the feature space. At this time, the control unit 701 projects the synthesized feature space from the projection direction parallel to the threshold plane, and a result of the projection of each defect candidate is placed on a two-dimensional plane. A distribution diagram of feature on this two-dimensional plane (hereinafter, referred to as a two-dimensional distribution diagram) is output to the display unit 702.

The two-dimensional distribution diagram here means a diagram where the distribution of defect candidates in the feature space is projected onto a two-dimensional plane in a direction parallel to the threshold plane from an arbitrary axis (a first axis) in the feature space (a two-dimensional plane formed by second and third axes different from the first axis). The term two-dimensional distribution diagram means that the diagram displayed on the display unit 702 is two-dimensional, and the number of axes of features included in the distribution diagram is the number of axes of features in the feature space (for example, three).

In the example of FIG. 7B, the two-dimensional distribution diagram represents the distribution of defect candidates in a three-dimensional feature space with three features as axes, and includes the axes of three features and a threshold plane represented in one dimension. More specifically, the two-dimensional distribution diagram represents the projection onto a feature 1 (1101)-feature 2 (1102) plane in a direction parallel to the threshold plane 1110 from the feature 3 (1103) axis. In this two-dimensional distribution diagram, three axes and the threshold plane 1110 represented in one dimension are displayed in the two-dimensional plane. Therefore, the user can recognize the association between the accuracy rate 1018 in FIG. 5 and the two-dimensional distribution diagram in FIG. 7B, and can easily determine whether the threshold (the threshold plane 1110) is appropriate.

Incidentally, as another example, a two-dimensional distribution diagram can be a projection onto a feature 2 (1102)-feature 3 (1103) plane from a direction of the feature (1101) axis, or can be a projection onto a feature 1 (1101)-feature 3 (1103) plane from a direction of the feature (1102) axis. These three types of two-dimensional distribution diagrams with different projection directions can be displayed simultaneously on the display unit 702, or any one type or arbitrarily-selected two types can be displayed simultaneously.

Here we explain advantages of the threshold setting using a two-dimensional distribution diagram. In a three-dimensional feature space, as shown in FIG. 7A, it is hard to determine either the upper area 1112 or the lower area 1113 a defect candidate located near the threshold plane 1110 is in. Furthermore, the distance between the position of a dot of each defect candidate and the threshold plane 1110 cannot be grasped, and it is hard to determine how much the threshold of each feature is to be adjusted. By using the two-dimensional distribution diagram in FIG. 7B, the user can grasp either the upper area 1112 or the lower area 1113 a defect candidate is in, and also can grasp the adjusting width of the threshold promptly.

In the example of FIG. 7B, with respect to the axes of two features (feature 1, feature 2), how far a distance a defect candidate is at from the axes of the features can be grasped. That is, the distance between the defect candidate and each of the axes of features 1 and 2 can be grasped to a certain degree, and how much the threshold is to be adjusted can be found.

In the example of FIG. 7B, for ease of explanation, it shows a state where necessary defect candidates and unnecessary defect candidates are clearly separated by the threshold plane 1110. However, actually, near the threshold plane 1110, necessary defect candidates and unnecessary defect candidates are mixed up. In the threshold setting in the defect judgement, there is difficulty that the threshold plane 1110 has to be set in a state where necessary defect candidates and unnecessary defect candidates are mixed up. In such a state, the setting of the threshold plane that increases the accuracy rate in FIG. 5 needs to be performed, so the display of the two-dimensional distribution diagram in FIG. 7B is particularly advantageous.

Incidentally, also in a case of using four or more features, a two-dimensional distribution diagram is effective. In this case, the feature-space creating unit 602 selects three features from four or more features, and creates a three-dimensional feature space. The control unit 701 only has to create a two-dimensional distribution diagram on the basis of the feature space. Therefore, even in the case of using four or more features, the two-dimensional distribution diagram can be displayed on the display unit 702. Conventionally, in the case of using four or more features, there arises a problem that how the four or more features are projected onto the screen of the display unit 702; however, according to the present embodiment, a two-dimensional distribution diagram is created after the creation of three-dimensional features, thereby this problem can be solved. Furthermore, when there are four or more features, by selecting three features more effective for defect judgement, accurate defect judgement is possible.

Figure 8A:
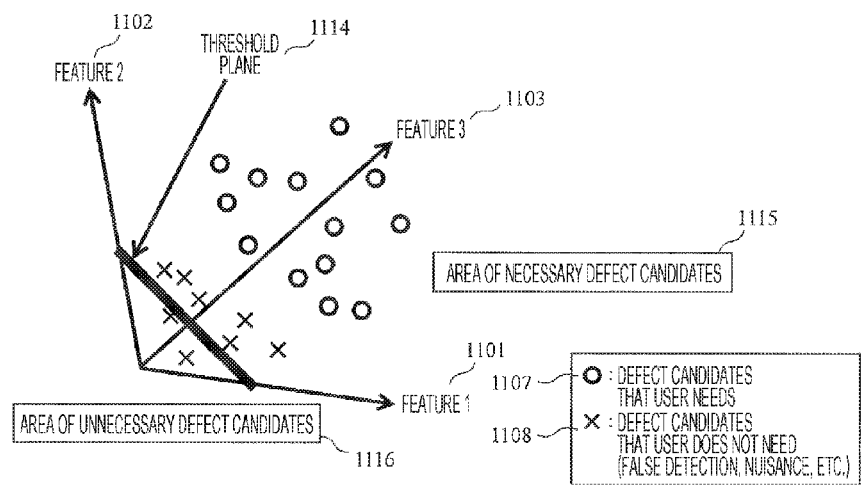
FIG. 8A is a two-dimensional distribution diagram showing the intermediate stage of setting the threshold in the first embodiment.
Figure 8B:
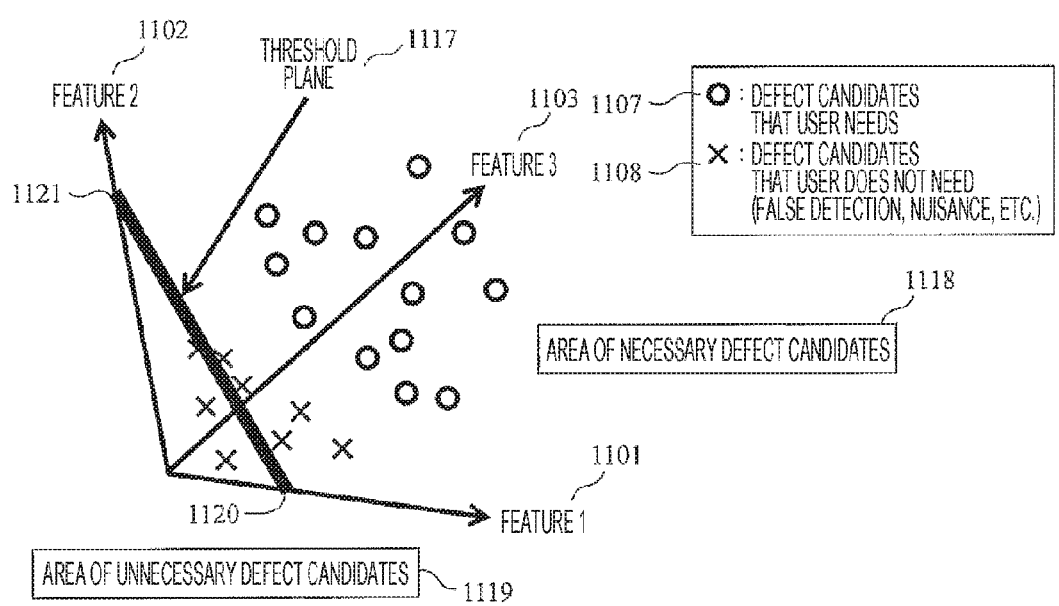
FIG. 8B is a two-dimensional distribution diagram showing the intermediate stage of setting the threshold in the first embodiment.
Figure 9:
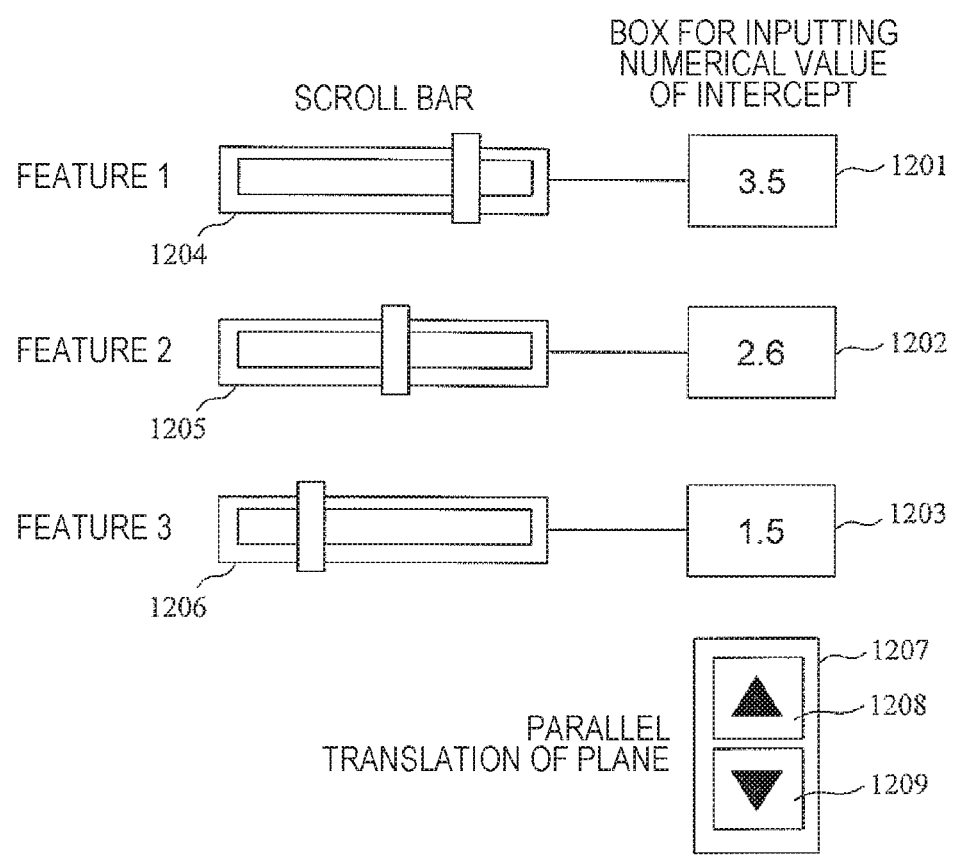
FIG. 9 is a diagram of a setting screen for the setting or adjustment of the threshold in the first embodiment.

FIGS. 8A and 8B are two-dimensional distribution diagrams showing the intermediate stage of the threshold setting. These diagrams are created by the control unit 701, and output to the display unit 702. FIG. 9 is a diagram of an input screen (a threshold change input unit) for the setting or adjustment of the threshold, and is a screen displayed on the display unit 702. The setting of the threshold (step 913) or the adjustment of the threshold (step 922) performed by the user is explained with FIGS. 7A to 9.

To look at the space separated by the threshold plane 1110 in FIG. 7B, there are defect candidates that the user needs in the area 1112 of necessary defect candidates, and there are defect candidates that the user does not need in the area 1113 of unnecessary defect candidates. This state is a state in which the accuracy rate 1018 in FIG. 5 is high. If the threshold is set in this state, the accurate (=a high accuracy rate) inspection can be performed. Incidentally, in FIG. 7B, for sake of simplicity of explanation, necessary defect candidates and unnecessary defect candidates are separated by the threshold plane 1110 without being mixed up; however, actually, necessary defect candidates and unnecessary defect candidates are mixed up near the threshold plane 1110.

On the other hand, in FIG. 8A, to look at a space separated by a threshold plane 1114, defects that the user does not need are included in an area 1115 of necessary defect candidates (in a state in which there are a lot of false detection), and the accuracy rate 1018 is decreased. From this two-dimensional distribution diagram, it can be determined that if this threshold plane 1114 is translated to the upper right, it becomes in a state in which the accuracy rate 1018 is high (FIG. 7B). The parallel translation of the threshold plane 1114 is made just by increasing the intercepts 1104, 1105, and 1106 in FIG. 7A by the equal magnification.

The screen of FIG. 9 can be displayed on the same screen as the two-dimensional distribution diagram, or can be displayed switching from the screen of the two-dimensional distribution diagram. When the screen of FIG. 9 is displayed on the same screen as the two-dimensional distribution diagram, the two-dimensional distribution diagram can be updated in real time according to the change of the threshold.

The screen of FIG. 9 includes boxes 1201, 1202, and 1203 for inputting numerical values of the intercepts, scroll bars 1204, 1205, and 1206 for adjusting the numerical values of the intercepts, and an up-down button 1207 for translating the threshold plane.

The user can translate the threshold plane 1114 by using virtually the same screen as that in FIG. 9. In this example, the intercept 1104 corresponds to the numerical value 1201, the intercept 1105 corresponds to the numerical value 1202, and the intercept 1106 corresponds to the numerical value 1203. The user can directly input numerical values obtained by increasing the values of the three intercepts 1104, 1105, and 1106 by the equal magnification to the boxes 1201, 1202, and 1203.

As another method, by using the up-down button (a parallel translation input unit) 1207, the threshold plane 1114 can be translated. The up-down button 1207 is composed of an up button 1208 and a down button 1209; when the up button 1208 is pressed, the numerical values of the boxes 1201, 1202, and 1203 are increased by the equal magnification (multiplied by a number larger than 1). Furthermore, when the down button 1209 is pressed, the numerical values of the boxes 1201, 1202, and 1203 are divided by an equal number (a number larger than 1).

When numerical values are directly input to the boxes 1201, 1202, and 1203, or when the intercepts are changed by using the up-down button 1207, the control unit 701 can display a new threshold plane using the values of the changed intercepts on the two-dimensional distribution diagram in FIG. 8B in real time. Incidentally, the control unit 701 can display the comparison table 1000 in FIG. 5 using the changed threshold plane at the same time.

Incidentally, the configuration of the screen of FIG. 9 is not limited to this. For example, the setting screen can include a button that increases or decreases the numerical values of the intercepts by a given width. Furthermore, the setting screen can include a box where a multiple number of the intercepts when translated is input.

FIG. 8A shows a state in which there are a lot of false detection; however, when the threshold plane 1114 is on the upper right than the threshold plane 1110 in FIG. 7A, defect candidates that the user needs are included in an area 1116 of unnecessary defect candidates (in a state in which there are a lot of overlooking of defect candidates that the user needs), and the accuracy rate 1018 is decreased. From this projected plan, the user can determine that if this threshold plane 1114 is translated to the lower left, it becomes in a state in which the accuracy rate 1018 is high (FIG. 7B). If the numerical values of the boxes 1201, 1202, and 1203 are changed to values obtained by dividing their numerical values by an equal number (a number larger than 1), the threshold plane 1114 is translated to the lower left. This parallel translation can be performed by directly changing the numerical values of the boxes 1201, 1202, and 1203, or can be performed by pressing the down button 1209 of the up-down button 1207.

In FIG. 8B, to look at a space separated by a threshold plane 1117, defect candidates that the user does not need are included in an area 1118 of necessary defect candidates (in a state in which there are a lot of false detection), and the accuracy rate 1018 is decreased. It can be determined that an intercept 1121 on the feature 2 (1102) axis is appropriate, though, an intercept 1120 on the feature 1 (1101) axis is inappropriate. From this two-dimensional distribution diagram, it can also be determined that by increasing the intercept 1120 on the feature 1 (1101), the threshold plane becomes an appropriate threshold plane.

The intercept 1120 on the feature 1 axis corresponds to the numerical value of the box 1201 in FIG. 9. The intercept 1120 can be changed by directly changing the numerical value of the box 1201, or the numerical value of the box 1201 can be changed by the scroll bar 1204. When the numerical value of the box 1201 has been changed, the control unit 701 displays the threshold plane using the value of the changed intercept on the two-dimensional distribution diagram in FIG. 8B in real time. When the box 1201 of the intercept has been changed, the tilt of the threshold plane 1117 on the feature space is changed, so the projection direction 1111 parallel to the threshold plane in FIG. 7A varies, and there arises the need to perform projection from a direction parallel to the new threshold plane. Accordingly, the control unit 701 projects defect candidates onto the two-dimensional plane from the direction parallel to the new threshold plane, and displays the updated two-dimensional distribution diagram on the display unit 702 in real time.

Here, there is described the case where the intercept on the feature 1 (1101) is inappropriate as an example; however, the same is true on a case where the intercept 1121 on the feature 2 (1102) axis is inappropriate. In this case, the threshold plane is set or adjusted by changing the numerical value of the box 1202. The scroll bar 1205 can be used in this change.

In FIG. 8B, whether or not the intercept on the feature 3 (1103) axis is appropriate cannot be determined; however, for example, by using a plan projected onto the feature 2 (1102)-feature 3 (1103) plane from the feature 1 (1101) axis, whether or not the intercept on the feature 3 (1103) axis is appropriate can be determined. When the intercept on the feature 3 (1103) axis is inappropriate, the numerical value of the box 1203 is changed. The scroll bar 1206 can be used in this change.

Incidentally, the adjustment of the threshold is not limited to the setting screen of FIG. 9. The two-dimensional distribution diagram can include an interface that can update the threshold plane by moving a given position in the threshold plane. Specifically, the two-dimensional distribution diagram can be provided with an interface enabling the user to drag an intercept of the threshold on any of the axes composing the three-dimensional feature space with the input unit 703 and move the intercept along the axis. To explain with the example of FIG. 8B, the user can drag the intercept 1120 with the input unit 703 such as a mouse and move the intercept 1120 to the right along the axis of feature 1.

Furthermore, the two-dimensional distribution diagram can include an interface that can translate the threshold plane. To explain with the example of FIG. 8A, the two-dimensional distribution diagram can be provided with an interface enabling the user to drag a position of about the center of the threshold plane 1114 with the input unit 703 such as a mouse and directly translate the threshold plane 1114 in an upper right direction.

By using a plan projected from a direction parallel to the threshold (a two-dimensional distribution diagram) in this way, a guideline for how the threshold is changed and how appropriate the threshold becomes can be provided to the user. Accordingly, the setting of the threshold is facilitated.

By referring to the two-dimensional distribution diagram, the user can easily grasp the association with the accuracy rate 1018 in FIG. 5 in step 915 of determining whether or not the threshold (the threshold plane) is appropriate. Furthermore, the control unit 701 can link the input on the setting screen in FIG. 9 with the display of the two-dimensional distribution diagram.

Moreover, in step 913 or step 922, when a new threshold has been input, steps 906 to 908 are performed each time it happens, and the control unit 701 outputs virtually the same table as the comparison table 1000 in FIG. 5 to the display unit 702. At soon as the new threshold is input, the result of inspection is updated, and the user can set the threshold while checking the accuracy rate 1018. The user can check if it is the threshold enabling the defect inspection to be performed with a high accuracy rate.

According to the present embodiment, it is possible to facilitate the setting or adjustment of the threshold plane used in the judgement for performing inspection, and even a less skilled user can perform the setting of the threshold. The setting or adjustment of the threshold plane is facilitated, thereby the time required to create a recipe for the inspection device can be shortened. Furthermore, a guideline for the setting or adjustment of the threshold plane can be obtained, so it is possible to perform the threshold setting with more accuracy (=a high accuracy rate). More accurate or stable defect inspection becomes possible, and, as a result, the accuracy of the yield management can be increased.

[Second Embodiment]

Subsequently, a second embodiment is described. In the following description, description of the same part as the first embodiment is omitted, and a different part from the first embodiment is described.

Figure 10:
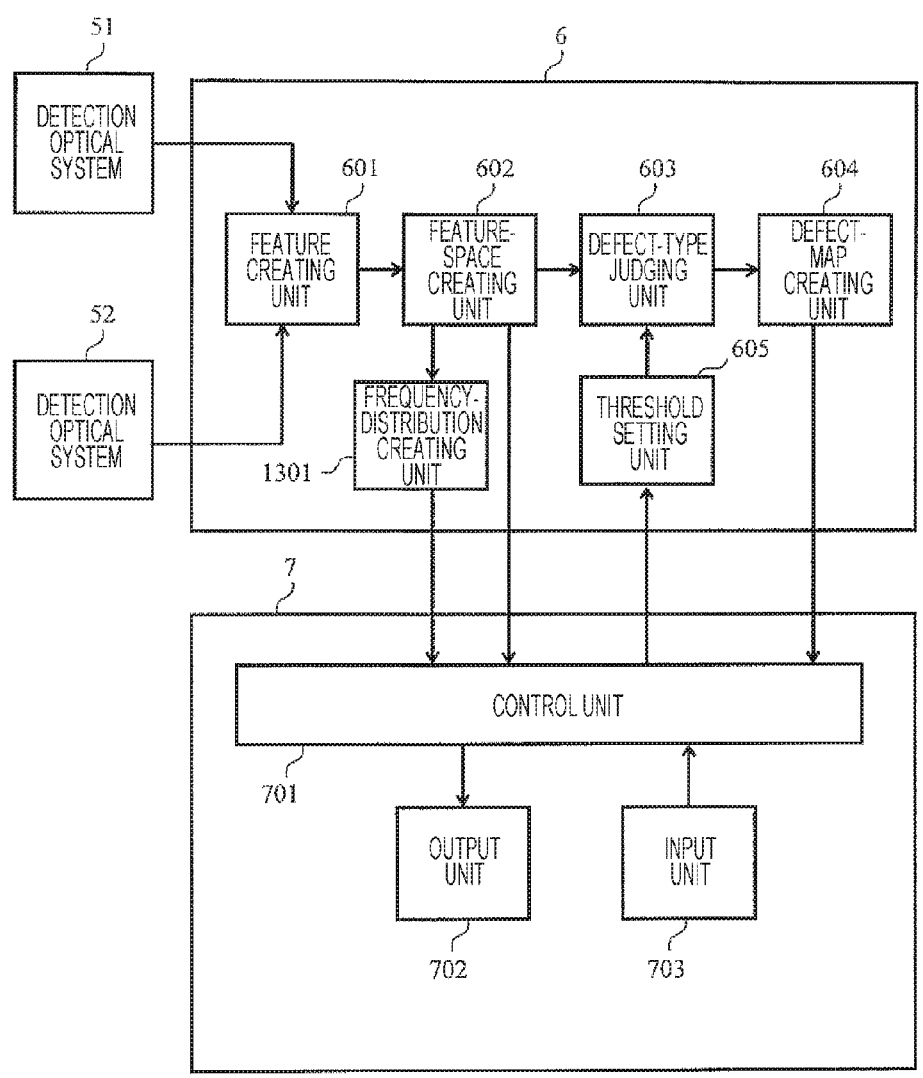
FIG. 10 is a block diagram showing a configuration of a part involved in defect inspection in a second embodiment.

FIG. 10 is a block diagram showing a configuration involved in defect inspection in the present embodiment. The processing system 6 includes a frequency-distribution creating unit 1301. The frequency-distribution creating unit 1301 receives a feature space from the feature-space creating unit 602, and creates a frequency distribution on the basis of the feature space.

In the present embodiment, in step 912 in FIGS. 4A and 4B, the control unit 701 outputs a frequency distribution diagram of defect candidates according to the distance from the threshold plane to the display unit 702, along with displaying a two-dimensional distribution diagram. The frequency distribution diagram here is a histogram showing the number of defect candidates in each interval according to the distance from the threshold plane in the two-dimensional distribution diagram.

Figure 11:
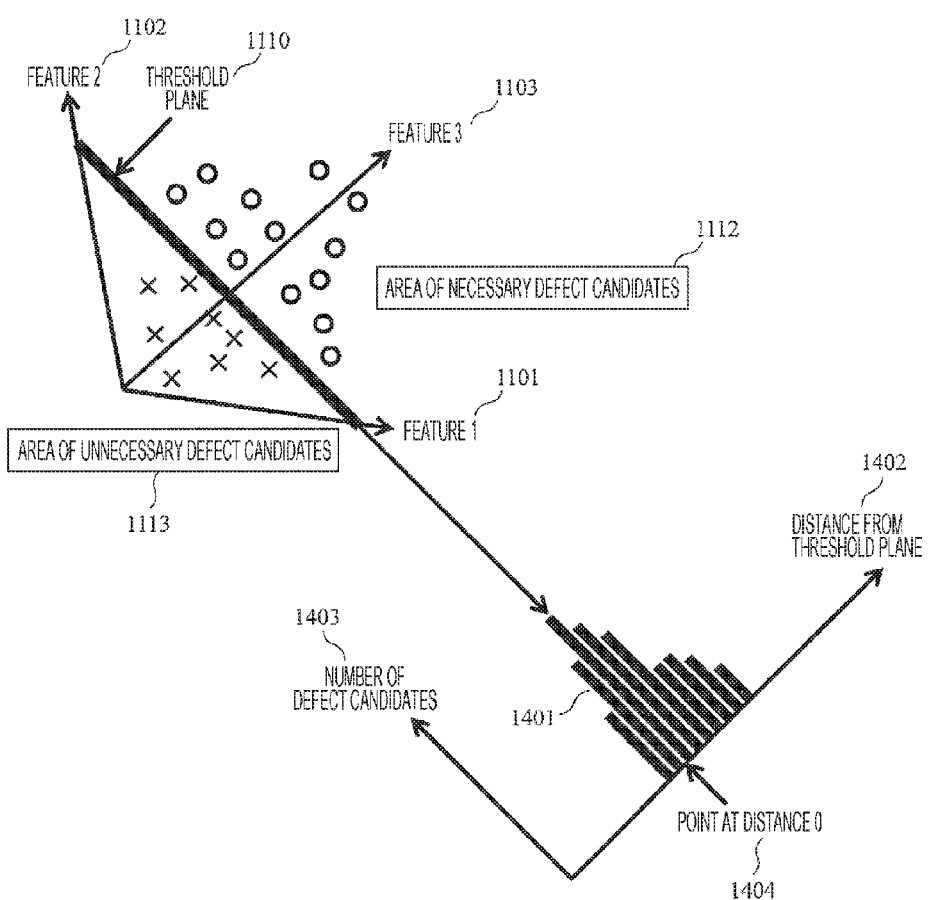
FIG. 11 is a two-dimensional distribution diagram and a frequency distribution diagram in the second embodiment.

FIG. 11 is a diagram explaining the present embodiment. As compared with the diagram in FIG. 7B, a two-dimensional distribution diagram shown in FIG. 11 is the same in the axes of features 1101, 1102, and 1103 and the threshold plane 1110, but differs in the distribution of defect candidates.

A frequency distribution diagram 1401 created by the frequency-distribution creating unit 1301 is a diagram where the distance (1402) from the threshold plane 1110 is set as the horizontal axis, and the number (1403) of defect candidates present in an arbitrary predetermined interval on the horizontal axis as the vertical axis. The height of a bar corresponds to the number of defect candidates present in an interval.

Furthermore, in the frequency distribution diagram 1401, an interval where the threshold plane is present, i.e., an interval including distance 0 (1404) from the threshold plane 1110 is highlighted. Moreover, the threshold plane 1110 on the two-dimensional distribution diagram (a projected plan) is associated with the interval including distance 0 (1404) from the threshold plane 1110. Accordingly, the user can confirm the position of the threshold plane 1110 in the frequency distribution diagram 1401. In FIG. 11, by extending an arrow from the threshold plane 1110 on the two-dimensional distribution diagram (the projected plan), the interval of distance 0 (1404) is indicated. As another example, the color of a bar indicating the interval of distance 0 (1404) can be set to be a different color from the color of the other intervals. Apart from that, the interval of distance 0 (1404) can be indicated by changing the width of the bar, or changing the pattern of the bar (for example, to a pattern of slanted lines), or things like that.

The number of defects on a sample that a defect inspection device in the present embodiment outputs is the number of defect candidates present in the area 1112 of necessary defect candidates separated by the threshold plane 1110. That is, in the frequency distribution diagram 1401 in FIG. 11, the sum of respective heights of bars present on the right side of the point 1404 of distance 0 on the frequency distribution is the number of defects.

Here we assume that the threshold plane 1110 is present in an area where the frequency distribution is dense, i.e., that the threshold plane 1110 is present in an area of which the height of a bar is greater than those of the other bars. On this assumption, if the frequency distribution is changed for some reasons (for example, the temporal change of an optical system), the number of defects output in defect inspection with respect to the same sample varies significantly before and after the change of the frequency distribution.

On the other hand, assume that the threshold plane is present in an area where the frequency distribution is sparse, i.e., that the threshold plane is present in an area of which the height of a bar is smaller than those of the other bars. On this assumption, if the frequency distribution is changed, there is no great change in the number of defects output in defect inspection with respect to the same sample before and after the change of the frequency distribution.

Therefore, when the user sets (step 913) or adjusts (step 922) the threshold (the threshold plane), by setting the threshold while checking this frequency distribution, a threshold with less change in the number of defects output in defect inspection with respect to the same sample can be selected. As a result, highly-reproducible defect inspection can be made.

In the above description, there is described the case where the right side of the threshold plane is the area of necessary defect candidates; however, there could be a case where the left side is the area of necessary defect candidates. In this case, the number of defects output from the device is the sum of respective heights of bars present on the left side of the interval of distance 0 (1404) on the frequency distribution. Also in this case, in regard to the variation in the number of defects, the same is true on the case where the right side is the area of necessary defect candidates.

Incidentally, defect information can be reflected in the frequency distribution diagram. In the two-dimensional distribution diagram, defect candidates determined to be necessary by the user are displayed by a mark (○), and defect candidates determined to be unnecessary by the user are displayed by a mark (×). The control unit 701 can acquire defect information and reflect the defect information in the colors of bars of intervals of the frequency distribution diagram. For example, as for bars of intervals, the proportion of defect candidates determined to be necessary by the user is indicated in a first color, and the proportion of defect candidates determined to be unnecessary by the user is indicated in a second color. By referring to this display, the user can easily determine whether the threshold plane 1110 is appropriate. In the example of FIG. 11, when the proportion of the first color is large on the right side of the interval of distance 0 (1404) and the proportion of the second color is large on the left side of the interval of distance 0 (1404), the user can determine that the threshold plane 1110 is appropriate. Incidentally, the reflection of defect information can be implemented by another method, such as by displaying by the proportion of a color pattern of a bar of each interval.

According to the present embodiment, the variation in the number of defects output is reduced, and stable yield management becomes possible.

[Third Embodiment]

Subsequently, a third embodiment is described. In the following description, description of the same part as the above embodiments is omitted, and a different part from the first and second embodiments is described.

Figure 12A:
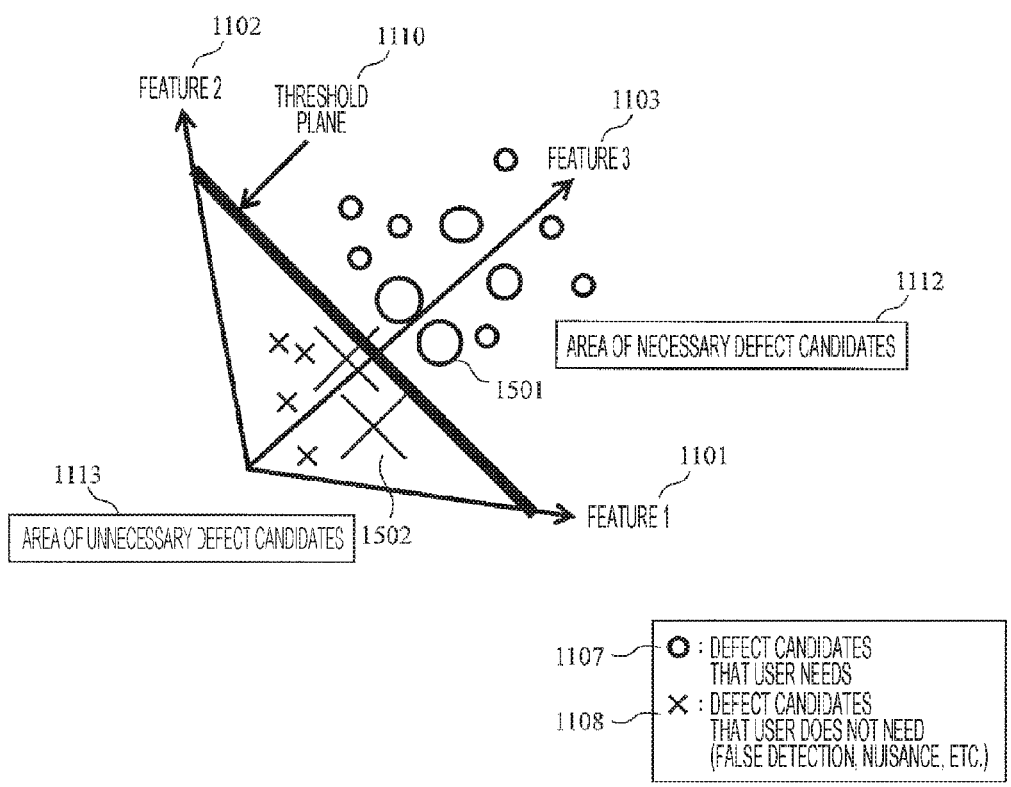
FIG. 12A is a two-dimensional distribution diagram in a third embodiment.
Figure 12B:
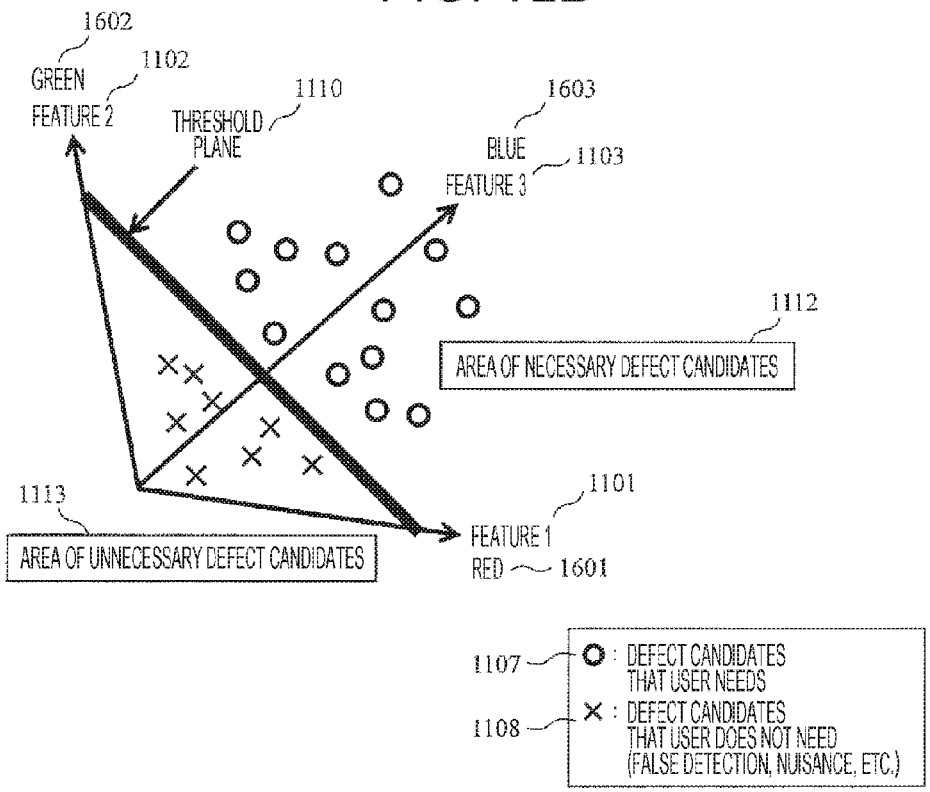
FIG. 12B is another example of the two-dimensional distribution diagram in the third embodiment.

FIGS. 12A and 12B are diagrams explaining the present embodiment. In the two-dimensional distribution diagram shown in FIG. 7B, information of the direction parallel to the threshold plane 1110 is ignored because it is projected onto the two-dimensional plane. Therefore, it is difficult to determine which intercept on a feature axis each defect candidate projected onto the two-dimensional plane is close to.

For the user to know which intercept on a feature axis each defect candidate is close to is important in setting (step 913) or adjusting (step 922) the threshold plane. This is because of the three intercepts defining the threshold, which intercept is to be adjusted depends on the distance from each intercept. For example, in defect candidates close to the intercept 1106 on the feature 3 (1103) axis, if defect candidates that the user does not need are included in the area 1112 of necessary defect candidates (if there are a lot of defect candidates detected falsely), by adjusting the intercept 1106 on the feature 3 (1103) axis, false detections can be reduced.

In the present embodiment, the control unit 701 calculates the distance of each defect candidate from an arbitrary feature axis, and displays a mark of the defect candidate with the size of the mark changed according to the calculated distance. In a two-dimensional distribution diagram of FIG. 12A, the distance from the intercept on the feature 3 (1103) axis is represented by the size of a placed mark of each defect candidate (○=1107, ×=1108). For example, defect candidates (for example, 1501, 1502) close to the intercept 1106 on the feature 3 (1103) axis are displayed in a larger size. Particularly, in this example, the user can determine the distance from the intercept 1106 on the feature (1103) axis from the size of the display of each defect candidate; the size of the display of each defect candidate can serve as a guideline for the setting or adjustment of the intercept 1106 of the feature 3 (1103) axis. At the same time, the distances from the intercept 1104 of the feature 1 (1101) axis and the intercept 1105 of the feature 2 (1102) axis can be determined; therefore, the three intercepts can be set or adjusted with one projected plan. Here, there is described the case where the feature 3 (1103) axis is on the near side as an example; however, a projected plan where the feature 1 (1101) axis or the feature 2 (1102) axis is on the near side can also be represented by the same method.

Another method for identifying the distance from a feature axis is explained with FIG. 12B. First, colors are assigned to features, respectively. In FIG. 12B, feature 1 (1101) is assigned red (1601), feature 2 (1102) is assigned green (1602), and feature 3 (1103) is assigned blue (1603). In the two-dimensional distribution diagram shown in FIG. 12B, the distances of each defect candidate from an intercept of each feature axis is represented on the basis of these color codes.

In the present embodiment, the control unit 701 calculates the distance of each defect candidate from an arbitrary feature axis, and displays a mark of the defect candidate with the color of the mark changed according to the calculated distance. For example, the proportion of red in a mark of each defect candidate is changed according to the distance from the intercept of the feature 1 (1101). For example, when the distance from the intercept of the feature 1 (1101) axis is small, the proportion of red is increased; when the distance is large, the proportion of red is reduced. Likewise, the proportion of green in a mark of each defect candidate is changed according to the distance from the intercept of the feature 2 (1102), and the proportion of blue in a mark of each defect candidate is changed according to the distance from the intercept of the feature 3 (1103). The control unit 701 specifies the color created in the proportion of these colors as a color representing a mark of each defect candidate, and outputs the mark of each defect candidate to the display unit 702.

Naturally, the way to assign colors is not limited to this. Which intercept of a feature axis each defect candidate is close to can be determined by these color codes; the color codes can serve as a guideline for the setting (step 916) or adjustment (step 915) of the threshold plane.

According to the present embodiment, when the user sets or adjusts the threshold plane for defect inspection, it is possible to facilitate the determination of which intercept on a feature axis its value is to be changed and how much the value is to be changed, and possible to shorten the time required to set the threshold.

[Fourth Embodiment]

Subsequently, a fourth embodiment is described. In the above embodiments, the defect determining method and the threshold setting method in defect inspection are described. The present embodiment is on "judgement of defect type (=defect classification)" where defects detected in the defect inspection are further classified. By performing the defect classification, more accurate yield management can be achieved. The defect classification includes, for example, classification of whether a defect is a foreign substance or a structural failure on a sample and classification of the type of a structural failure on a sample.

A method of determining the defect type is a method using a threshold (=a boundary plane) on a feature space set by a user or a device in advance, and is the same method as those described in the first to third embodiments. That is, the threshold setting methods described in the first to third embodiments can be applied to the threshold setting (=the setting of a boundary plane) in a device that performs defect classification described in the fourth embodiment. In a case of classifying two defect types, the methods in the first to third embodiments can be applied directly.

Furthermore, even when the number of defect types is three or more, multiple threshold planes (=boundary planes) for classification of defect types should be set. Even in the case of setting multiple threshold planes, a method of setting each of the threshold planes (=boundary planes) is the same as the case of classifying two defect types. Therefore, the methods in the first to third embodiments can be applied to the case of setting each of the threshold planes. In this case, multiple threshold planes represented in one dimension are displayed on a two-dimensional distribution.

In the following description, description of the same part as the above embodiments is omitted, and a different part from the first to third embodiments is described.

Figure 13:
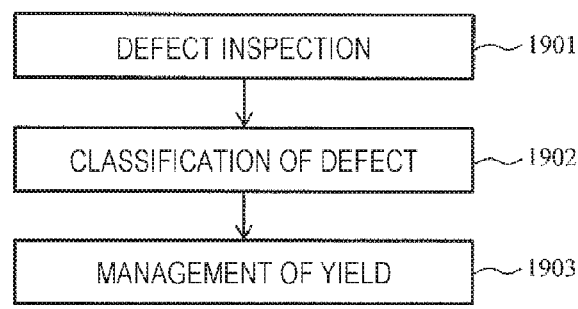
FIG. 13 is a flow diagram showing the yield management of defect classification according to a fourth embodiment.

FIG. 13 is a defect inspection flow diagram explaining what kind of position the defect classification is in the yield management. First, a sample is inspected for any defect thereon (1901). Defects detected by the inspection are classified by the defect type (1902). Using a result of the classification, the user performs the yield management of sample products (1903). By performing the classification of defects (1902) here, more accurate yield management than that in a case of no defect classification performed can be performed.

Figure 14:
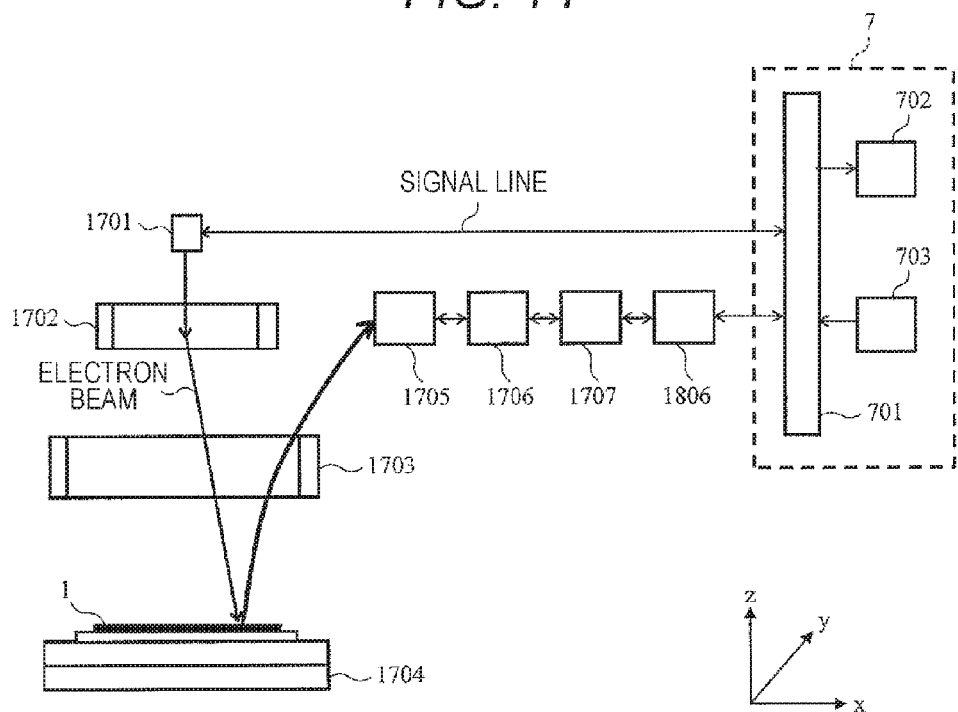
FIG. 14 is a block diagram showing a schematic configuration of an observation device in the fourth embodiment.

FIG. 14 is a diagram showing a configuration of an observation device that performs the defect classification in the present embodiment. As an example of the observation device, an observation device using an electron beam source is explained. Here, an observation device using an electron source is explained; however, an observation device using light or charged particle radiation other than that can also be applied.

The observation device includes an electron optical system. The electron optical system includes an electron source 1701, a deflector 1702, and an objective lens 1703. The electron optical system can include other components other than these, and is not limited to these. The observation device further includes a detection system. The detection system includes a detector 1705, an A/D converter 1706, and an image processing unit 1707.

An electron beam from the electron source 1701 is deflected in an x direction by the deflector 1702, and a sample 1 is irradiated with the electron beam through the objective lens 1703. As soon as the sample 1 is irradiated with the electron beam, a stage 1704 is continuously moved in a y direction. At this time, a secondary electron from the sample 1 is detected by the detector 1705. Then, the A/D converter 1706 converts a detection signal from the detector 1705, and the image processing unit 1707 converts a converted digital signal into an image. After that, the image processing unit 1707 inputs the image to a processing unit 1806. This observation device can be an observation device using a light source instead of an electron source. Furthermore, observation of defects can also be made by using images acquired from the detection optical systems 51 and 52 in the device configuration in FIG. 1.

Figure 15:
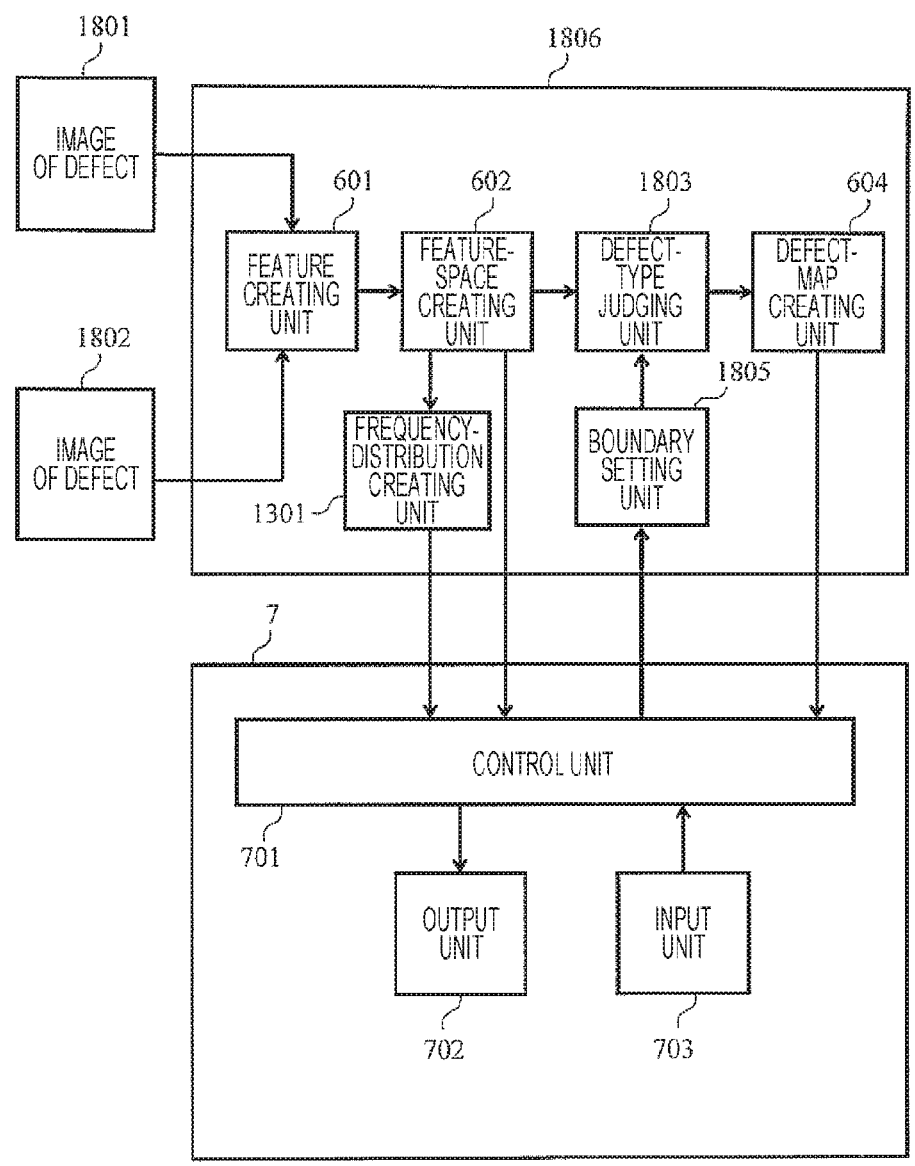
FIG. 15 is a block diagram showing a configuration of a part involved in the defect classification in the fourth embodiment.

FIG. 15 is a block diagram showing a configuration involved in the defect classification in the present embodiment. The processing unit 1806 includes a defect-type judging unit 1803 and a boundary setting unit 1805. The boundary setting unit 1805 receives a boundary plane (a threshold plane) for classification of the defect type from the control unit 701, and outputs the boundary plane to the defect-type judging unit 1803. The defect-type judging unit 1803 performs a defect classifying process on the basis of the received boundary plane.

Figure 16:
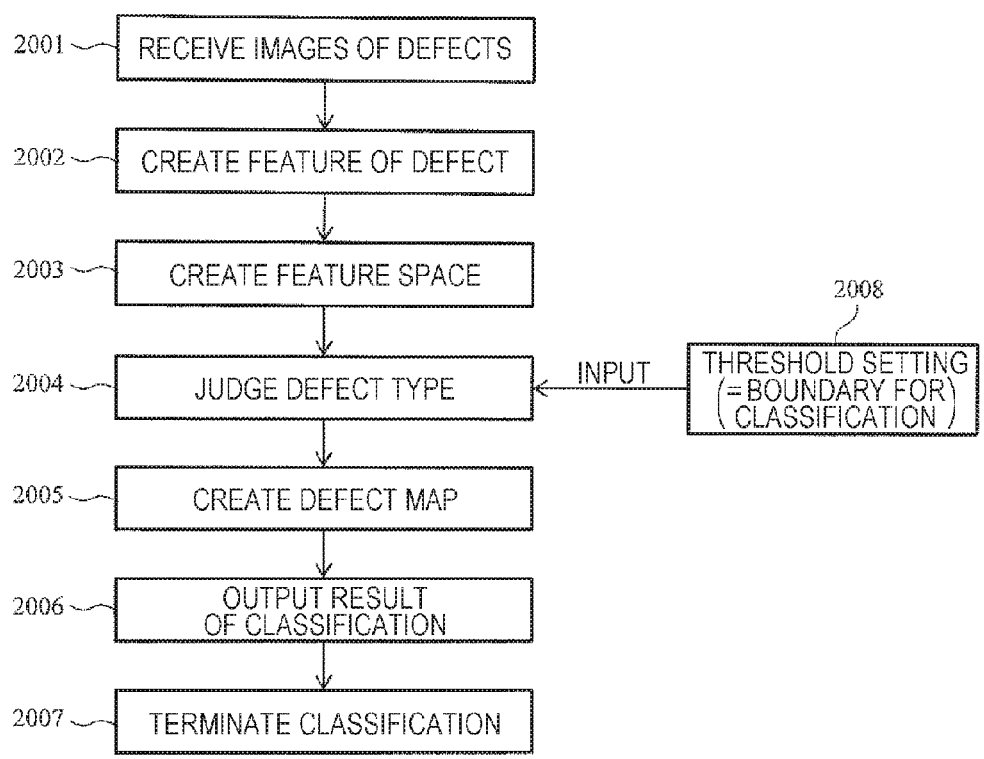
FIG. 16 is a flow diagram of the defect classification in the fourth embodiment.

FIG. 16 is a flow diagram of the defect classification in the fourth embodiment. First, the processing unit 1806 receives images 1801 and 1802 of defects from the detection system (the image processing unit 1707) (2001). The images 1801 and 1802 of defects can be an image from the observation device using electron beams in FIG. 14, or can be an image output from the detection optical system in FIG. 1. Or, the images 1801 and 1802 of defects can be an image from another type of observation device. FIG. 15 is the configuration in which two images 1801 and 1802 are received; however, the number of images received can be one, or can be three or more.

Next, the feature creating unit 601 creates a feature of each defect on the basis of the images 1801 and 1802 (2002). Next, the feature-space creating unit 602 creates a feature space using the created feature of the defect (2003).

Next, at least one boundary plane (threshold plane for classification) is set by use of the input unit 703 and the display unit 702 of the control system 7 (2008). This boundary plane can be manually set by the user, or can be automatically set by the control unit 701 as described above. The flow of the setting is the same as FIG. 4A or 4B. At this time, the boundary setting unit 1805 receives the boundary plane (the threshold plane) for classification of the defect type from the control unit 701, and outputs the boundary plane to the defect-type judging unit 1803.

Next, the defect-type judging unit 1803 judges the defect type using the boundary plane set in step 2008 (2004). Next, the defect-map creating unit 604 creates a defect map on the basis of a result of the judgement of the defect type (2005). The defect map here is information in which a defect is associated with the type of the defect on the map.

Next, the control unit 701 receives the defect map, and outputs a result of the classification to the display unit 702 (2006). Here, if the result of classification is not appropriate, the adjustment of the boundary plane is performed, just like FIGS. 4A and 4B. This adjustment is repeated until it has been determined that the boundary plane is appropriate. When it has been determined to be appropriate, the classification of the defect type is terminated (2007).

According to the present embodiment, it is possible to facilitate the setting or adjustment of the threshold plane (=the boundary plane for classification) used in the judgement for defect classification, and even a less skilled user can perform the setting of the threshold. The setting or adjustment of the threshold plane is facilitated, thereby the time required to create a recipe for performing the classification can be shortened. Furthermore, a guideline for the setting or adjustment of the threshold plane can be obtained, so it is possible to perform the threshold setting with more accuracy (=a high accuracy rate). More accurate defect classification becomes possible, and, as a result, the accuracy of the yield management can be increased.

The display methods and the threshold setting methods described in all the above embodiments can also be applied to inspection devices and observation devices other than those described in the embodiments.

Incidentally, the present invention is not limited to the above embodiments, and includes various variations. For example, the above embodiments are described in detail to explain the present invention in ways easy to understand, and do not necessarily include all the described configurations. Furthermore, part of the configuration of one embodiment may be replaced with the configuration of another embodiment, or the configuration of one embodiment can be added with the configuration of another embodiment. Moreover, part of the configuration of each embodiment can be subjected to the addition, elimination, and replacement with the configuration of another embodiment.

In terms of the fact that the relationship between the threshold and the distribution of defect candidates can be grasped and the setting or adjustment of the threshold is facilitated, the present invention can be implemented as a display device that displays information of defect candidates from a defect inspection device. The display device includes a display unit that displays thereon a setting screen for setting a threshold for judgement of defect candidates. The setting screen is a two-dimensional distribution diagram that represents the distribution of defect candidates in a three-dimensional feature space with three features as axes and includes the axes of three features and the threshold represented in one dimension.

Functions of the processing system 6, the control unit 701, etc. in the embodiments can be realized by program codes of software. In this case, a recording medium with the program codes recorded thereon is provided to a system or a device, and a computer (or a CPU or an MPU) of the system or device reads out the program codes stored in the recording medium. In this case, the program codes read out from the recording medium realize the above-mentioned functions of the embodiments, and the program codes and the recording medium having stored therein the program codes compose the present invention. As recording media for supplying such program codes, for example, flexible disks, CD-ROMs, DVD-ROMs, hard disks, optical disks, magneto-optic disks, CD-Rs, magnetic tapes, nonvolatile memory cards, ROMs, etc. are used.

Last, the processes and techniques described here are not essentially related to any particular device, and can be implemented by any suitable combination of components. Furthermore, general-purpose, various types of devices can be used. For executing steps of the method described here, it may be beneficial to construct a dedicated device. That is, some or all of various functions of the processing system 6 and the control unit 701 can be realized by hardware using electronic components such as an integrated circuit.

Moreover, in the above embodiment, control lines and information lines considered to be necessary for sake of explanation are shown, and all the control lines and information lines of products are not necessarily shown. All the configurations can be connected reciprocally.

REFERENCE SIGNS LIST

1 sample
2 stage
3 wafer conveying system
4 illumination optical system
6 processing system (defect detecting unit)
7 control system
51 detection optical system
52 detection optical system
511 objective lens
512 spatial filter
513 imaging lens
514 sensor
521 objective lens
522 spatial filter
523 imaging lens
524 sensor
601 feature creating unit
602 feature-space creating unit
603 defect judging unit
604 defect-map creating unit
605 threshold setting unit
701 control unit
702 display unit
703 input unit
1301 frequency-distribution creating unit
1701 electron source
1702 deflector
1703 objective lens
1704 stage
1705 detector
1706 A/D converter
1707 image processing unit
1803 defect-type judging unit
1805 boundary setting unit
1806 processing unit (defect classifying unit)

The invention claimed is:

1. A defect inspection device, comprising:
an illumination optical system that irradiates a sample with a light or an electron beam;
a detector that detects a signal obtained from the sample by irradiation with the light or the electron beam;
a defect detecting unit that detects defect candidates on the sample by comparing a signal output from the detector with a predetermined threshold; and
a display unit that displays a setting screen for setting the threshold,
wherein the setting screen is a two-dimensional distribution diagram that represents a distribution of defect candidates in a three-dimensional feature space with three features as axes and includes the axes of three features and the threshold represented in one dimension.

2. The defect inspection device according to claim 1, wherein
the threshold is defined by a two-dimensional plane in the three-dimensional feature space, and
the two-dimensional distribution diagram is what the distribution of defect candidates in the feature space is projected onto a two-dimensional plane in a direction parallel to the two-dimensional plane of the threshold.

3. The defect inspection device according to claim 2, wherein
the defect candidates displayed in the two-dimensional distribution diagram have been judged to be either a defect to be detected or a defect not to be detected by a user in advance, and
the threshold divides the feature space in two.

4. The defect inspection device according to claim 2, wherein the display unit displays thereon a threshold change input unit for changing a position of the threshold on the two-dimensional distribution diagram together with the two-dimensional distribution diagram.

5. The defect inspection device according to claim 4, wherein the display of the position of the threshold on the two-dimensional distribution diagram is updated in real time according to content input to the threshold change input unit.

6. The defect inspection device according to claim 4, wherein the threshold change input unit includes a parallel translation input unit that translates the threshold on the two-dimensional distribution diagram.

7. The defect inspection device according to claim 2, wherein the two-dimensional distribution diagram includes an interface that enables the threshold to be updated by moving a predetermined position of the threshold.

8. The defect inspection device according to claim 7, wherein the interface includes at least either one of:
a first interface enabling an intercept of the threshold on any of the exes composing the three-dimensional feature space to be moved; and
a second interface enabling the threshold represented in one dimension to be translated.

9. The defect inspection device according to claim 4, wherein when tilt of the threshold on the two-dimensional distribution diagram is changed, the display unit updates the two-dimensional distribution diagram with a new two-dimensional distribution diagram projected in a direction parallel to the two-dimensional plane of the changed threshold in the feature space.

10. The defect inspection device according to claim 4, wherein
the display unit displays thereon a comparison table including the number of defects determined to be a defect to be detected or a defect not to be detected by the user in advance and the number of defects automatically judged to be a defect to be detected or a defect not to be detected by the threshold, and
the display unit updates the comparison table according to a change of the threshold.

11. The defect inspection device according to claim 1, wherein the display unit further displays thereon a histogram showing the number of defect candidates in each interval according to a distance from the threshold in the two-dimensional distribution diagram.

12. The defect inspection device according to claim 11, wherein the histogram is what an interval including data resulting in a distance of 0 from the threshold to a defect candidate is highlighted, or the interval is associated with the display of the threshold on the two-dimensional distribution diagram.

13. The defect inspection device according to claim 1, wherein
the threshold is defined by a two-dimensional plane in the three-dimensional feature space, and
size or color of a mark representing each defect candidate on the two-dimensional distribution diagram is determined according to a distance from an intercept of the threshold on any of the axes composing the three-dimensional feature space to the defect candidate.

14. The defect inspection device according to claim 13, wherein
the axes composing the three-dimensional feature space are associated with different colors, respectively, and
the color of a mark representing each defect candidate on the two-dimensional distribution diagram represents distances from the axes composing the three-dimensional feature space.

15. A display device for displaying information of defect candidates from a defect inspection device, the display device comprising a display unit that displays thereon a setting screen for setting a threshold for judgement of defect candidates,
wherein the setting screen is a two-dimensional distribution diagram that represents a distribution of defect candidates in a three-dimensional feature space with three features as axes and includes the axes of three features and the threshold represented in one dimension.

16. A defect inspection device, comprising:
an illumination optical system that irradiates a sample with a light or an electron beam;
a detector that detects a signal obtained from the sample by irradiation with the light or the electron beam;
a defect classifying unit that classifies a defect on the sample by comparing a signal output from the detector with at least one threshold; and
a display unit that displays a setting screen for setting the threshold,
wherein the setting screen is a two-dimensional distribution diagram that represents a distribution of defect candidates in a three-dimensional feature space with three features as axes and includes the axes of three features and the threshold represented in one dimension.

* * * * *